US007928192B2

(12) United States Patent
Masignani et al.

(10) Patent No.: US 7,928,192 B2
(45) Date of Patent: Apr. 19, 2011

(54) ADP-RIBOSYLATING BACTERIAL TOXINS

(75) Inventors: Vega Masignani, Siena (IT);
Mariagrazia Pizza, Siena (IT); Rino Rappuoli, Castelnuovo Berardenga (IT)

(73) Assignee: Novartis AG, Basel (CH)

( * ) Notice: Subject to any disclaimer, the term of this patent is extended or adjusted under 35 U.S.C. 154(b) by 750 days.

(21) Appl. No.: 10/472,681

(22) PCT Filed: Mar. 28, 2002

(86) PCT No.: PCT/IB02/02080
§ 371 (c)(1),
(2), (4) Date: Sep. 2, 2004

(87) PCT Pub. No.: WO02/079242
PCT Pub. Date: Oct. 10, 2002

(65) Prior Publication Data
US 2006/0057155 A1    Mar. 16, 2006

(30) Foreign Application Priority Data

Mar. 30, 2001 (GB) .................................. 0108024.1

(51) Int. Cl.
*C07K 1/00* (2006.01)
(52) U.S. Cl. ........................................ 530/350; 530/300
(58) Field of Classification Search ........................ None
See application file for complete search history.

(56) References Cited

U.S. PATENT DOCUMENTS 7,115,730 B1 * 10/2006 Pizza et al. ................... 536/23.7
2006/0269563 A1   11/2006 Pizza et al.

FOREIGN PATENT DOCUMENTS

| WO | WO 95/17211     | 6/1995  |
| WO | 00/71725 A2     | 11/2000 |
| WO | WO-02/079242 A2 | 10/2002 |

OTHER PUBLICATIONS

Seffernick et al. (J. Bacteriology, vol. 183, pp. 2405-2410, 2001.*
(Wells, Biochemistry, vol. 29, pp. 8509-8517, 1990).*
Tettelin et al. (Science, vol. 287, pp. 1809-1815, 2000).*
Database Accession No. AX236858, last updated Sep. 26, 2001, located at www.ncbi.nlm.nih.gov/entrez/viewer.fcgi?db=nuccore&id=15796444>, last visited on Jan. 26, 2009.
Devos et al., Practical limits of function prediction. Proteins: Structure, Function, and Genetics. 2000, vol. 41: 98-107.
Freytag, LC. et al. (1999). "Bacterial Toxins as Mucosal Adjuvants," *Current Topics in Microbiology and Immunology* 236:215-236.
Glenn, G. et al. (1999). "Advances in Vaccine Delivery: Transcutaenous Immunisation," *Expert Opinion on Investigational Drugs* 8(6):797-805.
International Search Report mailed on Jan. 12, 2004, for PCT Application No. PCT/IB03/04295 filed on Sep. 1, 2003.
International Search Report mailed on Jul. 31, 2003, for PCT Application No. PCT/IB02/02080 filed on Mar. 28, 2002.
Scharton-Kersten, T. et al. (2000). "Transcutaneous Immunization with Bacterial ADP-Ribosylating Exotoxins, Subunits, and Unrelated Adjuvants," *Infection and Immunity* 68(9):5306-5313.
United States Office Action mailed on May 5, 2010, for U.S. Appl. No. 10/526,125, filed Sep. 1, 2003.
Whisstock, J.C. et al. (Aug. 2003). "Prediction of Protein Function from Protein Sequence and Structure," *Quarterly Review of Biophysics* 36(3):307-340.
Allured et al. (1986). "Structure of exotoxin A of *Pseudomonas aeruginosa* at 3.0-Angstrom Resolution," *Proceedings of the National Academy of Sciences*, USA, 83:1320-1324.
Antoine et al. (1993). "Evidence for a Catalytic Role of Glutamic Acid 129 in the NAD-glycohydrolase Activity of the Pertussis Toxin S1 Subunit," *The Journal of Biological Chemistry*, 268(32):24149-24155.
Barbieri et al. (1989). "Photolabeling of Glu-29 of the S-1 Subunit of Pertussis Toxin with NAD," *Infection and Immunity*, 57(11):3549-3554.
Broun et al. (1998). "Catalytic plasticity of fatty acid modification enzymes underlying chemical diversity of plant lipids," *Science*, 282:1315-1317.
Burnette et al. (1988). "Pertusssi Toxin S1 Mutant with Reduced Enzyme Activity and a Conserved Protective Epitope," *Science*, 242(4875):72-74.
Carroll et al. (1984). "NAD Binding Site of Diphtheria Toxin: Identification of a Residue Within the Nicotinamide Subsite by Photochemical Modification With NAD," *Proceedings of the National Academy of Sciences*, USA, 81;3307-3311.
Domenighini et al. (1994). "Common Features of the NAD-binding and Catalytic Site of ADP-ribosylating Toxins," *Molecular Microbiology*, 14(1):41-50.
Douglas et al. (1987). "Exotoxin A of *Pseudomonas aeruginosa*: Substitution of Glutamic Acid 553 with Aspartic Acid Drastically Reduces Toxicity and Enzymatic Activity," *Journal of Bacteriology*, 169(11):4967-4971.
Douglas et al. (1990). "*Pseudomonas aeruginosa* Exotoxin A: Alterations of Biological and Biochemical Properties Resulting from Mutation of Glutamic Acid 553 to Aspartic Acid," *Biochemistry*, 29(21):5043-5049.
Kisseley, L. (2002). "Polypeptide release factors in prokaryotes and eukaryotes: same function, different structure," *Structure* 10:8-9.
Lobet et al. (1991). "Effect of Site-Directed Mutagenic Alterations on ADP-Ribosyltransferase Activity of the A Subunit of *Escherichia coli* Heat-Labile Enterotoxin," *Infection and Immunity*, 59(9):2870-2879.
Pizza et al. (1988). "Subunit S1 of pertussis toxin: Mapping of the Regions Essential for ADP-ribosyltransferase Activity," *Proceedings of the National Academy of Sciences*, USA, 85:7521-7525.
Rappuoli et al. (1991). "Structure and Evolutionary Aspects of ADP-ribosylating Toxins," in *Bacterial Protein Toxins*. Alouf, J.E., Freer, J.H. (eds., London: Academic Press. p. 12.
Response to United States Office Action mailed on Jan. 11, 2008, for U.S. Appl. No. 10/526,125, filed Sep. 1, 2003.
Response to United States Office Action mailed on May 24, 2007, for U.S. Appl. No. 10/526,125, filed Sep. 1, 2003.

(Continued)

*Primary Examiner* — Hope A Robinson
(74) *Attorney, Agent, or Firm* — Amy Hessler; Otis Littlefield

(57) ABSTRACT

ADP-ribosylating toxins from *Neisseria meningitidis, Streptomyces coelicolor, Mycoplasma pneumoniae, Salmonella typhimurium, Salmonella paratyphi*, and *Streptococcus pyogenes* are disclosed, together with mutant toxins and uses therefor. There is only a low level of sequence identity between these toxins and toxins such as cholera toxin and *E. coli* heat labile toxin.

5 Claims, 3 Drawing Sheets

OTHER PUBLICATIONS

Response to United States Office Action mailed on May 7, 2009, for U.S. Appl. 10/526,125, filed Sep. 1, 2003.
Response to United States Office Action mailed on Sep. 17, 2008, for U.S. Appl. No. 10/526,125, filed Sep. 1, 2003.
Seffernick et al. (2001). "Melamine deaminase and Atrazine chlorohydrolase: 98 percent identical but functionally different," *Journal of Bacteriology* 183(8):2405-2410.
Thanabalu et al. (1991). "Cloning, Sequencing, and Expression of a Gene Encoding a 100-Kilodalton Mosquitocidal Toxin from *Bacillus sphaericus* SSII-1," *Journal of Bacteriology*, 173(9):2776-2785.
Tsuji et al. (1991). "Glutamic Acid-112 of the A Subunit of Heat-Labile Enterotoxin From Enterotoxigenic *Escherichia coil* is Important for ADP-ribosyltransferase Activity," *FEBS*, 291 (2):319-321.
Tweten et al. (1985). "Diphtheria Toxin: Effect of Substituting Aspartic Acid for Glutamic Acid 148 on ADP-Ribosyltransferase Activity," *The Journal of Biological Chemistry*, 260(19):10392-10394.
United States Office Action mailed on Aug. 4, 2009, for U.S. Appl. No. 10/526,125, filed Sep. 1, 2003.
United States Office Action mailed on Dec. 29, 2006, for U.S. Appl. No. 10/526,125, filed Sep. 1, 2003.
United States Office Action mailed on Jul. 11, 2007, for U.S. Appl. No. 10/526,125, filed Sep. 1, 2003.
United States Office Action mailed on Mar. 17, 2008, for U.S. Appl. No. 10/526,125, filed Sep. 1, 2003.
United States Office Action mailed on Nov. 7, 2008, for U.S. Appl. No. 10/526,125, filed Sep. 1, 2003.
Wilson et al. (1990). "Active-Site Mutations of Diphtheria Toxin: Effects of Replacing Glutamic Acid-148 with Aspartic Acid, Glutamine, or Serine," *Biochemistry* 29:8643-8651.
Wishart et al. (1995). "A single mutation converts a novel phosphotyrosine binding domain into a dual-specificity phosphatase," *Journal of Biological Chemistry* 270(45):26782-26785.
Witkowski et al. (1999). "Conversion of b-ketoacyl synthase to a Malonyl Decarboxylase by replacement of the active cysteine with glutamine," *Biochemistry* 38:11643-11650.
Ala'Aldeen et al., "Cloning, sequencing, characterization and implications for vaccine design of the novel dihydrolipoyl acetyltransferase of Neisseria Meningitidis," J. Medical Microbiology 45:419-432, 1996.
Database EMBL accession No. AE002482, "N. meningitides serogrop B strain MC58 section 124 of 206 of the complete genome," Mar. 15, 2000.
Database SWALL accession No. Q91Z10, "Hypothetical protein NMB 1343," Oct. 15, 2000.
Database EMBL accession No. X82637, "N. meningitides pdh gene cluster," Nov. 25, 1994.
Database EMBL accession No. X77920, "N. meningitides outer membrane protein P64K (pm-6) gene," Mar. 8, 1994.
Database EMBL accession No. AAA81487, "N. meningitides partial DNA sequence gnm_35 SEQ ID No. 35," Dec. 4, 2000.
Database EMBL accession No. AX044032, "Neisseria genomic sequences; sequence 111," Nov. 24, 2000.
Database EMBL accession No. CAA41592, "Cholera toxin A protein (CTA)," Mar. 25, 1991.
Database EMBL accession No. AAY966654, "Plant-optimized mutant V. cholera toxin subunit K63", Jun. 2000.
Giudice et al., "Genetically derived toxoids for use as vaccines and adjuvants," Vaccine 17:S44-S52, 1999.
Krueger et al., "The family of bacterial ADP-ribosylating exotoxins," Clinical Microbiology Reviews 8:34-47, 1995.
Tettelin et al., "Complete Genome sequence of Neisseria Meningitidis serogroup B strain MC58." Science 287:1809-1815, 2000.
Response to United States Office Action mailed on Feb. 1, 2010, for U.S. Appl. No. 10/526,125, filed Sep. 1, 2003.

* cited by examiner

FIGURE 1

CT group ★

Region 1

| | | |
|---|---|---|
| CT | $^{1}$IYRA$^{8}$ | |
| NMB1343 | $^{1}$IYRA$^{8}$ | |
| LT | $^{1}$IYRA$^{8}$ | |
| LT-II | $^{1}$FFRA$^{6}$ | |
| PT | $^{7}$VYRY$^{10}$ | |
| ExoS | — | |
| C2_bot | $^{97}$AYRR$^{100}$ | |
| C3_bot | $^{86}$LFRG$^{89}$ | |
| C3_II | $^{86}$IFRG$^{89}$ | |
| C3_lim | $^{86}$LFRG$^{89}$ | |
| IOTA_tox | $^{204}$VYRR$^{207}$ | |
| B cereus | | |
| Edin | $^{118}$VYRL$^{121}$ | |

Region 2

| | |
|---|---|
| $^{55}$HDDGYVSTSISLRSAHLVGQTI$^{76}$ | |
| $^{64}$LDGGYISTSLDKETAKFFAE$^{85}$ (shaded) | |
| $^{55}$YDDGYVSTSLSLRSAHLAGQSI$^{76}$ | |
| $^{53}$YNDGYVSTTVTLRQAHLIGQNI$^{74}$ | |
| $^{55}$FVSTSSSRRYTEVYLERRMQE$^{76}$ | |
| $^{338}$DDGYLSTSLNPGVARSGQGTI$^{358}$ | |
| $^{345}$SFSTSLKSTPLSFS$^{359}$ | |
| $^{131}$GYISTSLMSAQFGGR$^{145}$ | |
| $^{131}$GYISTSLMNVSQFAG$^{145}$ | |
| $^{131}$GYISTSLVNGSAFAGR$^{147}$ | |
| $^{336}$FISTSIGSVNMSAFAKRKI$^{354}$ | |
| $^{170}$GYSSTQLVSGAAVGGR$^{185}$ | |

Region 3

| |
|---|
| $^{107}$HPDEQEVSAL$^{116}$ |
| $^{107}$PNERAVTQ (shaded) |
| $^{107}$HPYEQEVSAL$^{116}$ |
| $^{106}$YPSENEFAAL$^{115}$ |
| $^{128}$TYQSEYL$^{130}$ |
| $^{375}$YKNEREILY$^{384}$ |
| $^{385}$EQEILLN$^{393}$ |
| $^{169}$FPGQLEVLLP$^{178}$ |
| $^{169}$FAGQLEMLLP$^{178}$ |
| $^{169}$FKGQLEVLLP$^{178}$ |
| $^{375}$YAGEYEVLL$^{383}$ |
| $^{210}$YGQQEVLLP$^{219}$ |
| ...YPGQYELLP... |

DT group ★

| | | |
|---|---|---|
| DT | $^{50}$SYHGT$^{23}$ | $^{15}$WKGFYSTDNKYDAAGY$^{30}$ | $^{14}$EYIN |
| PAETA | $^{468}$GYHGT$^{442}$ | $^{166}$WRGFYIAGDPALAYDY$^{181}$ | $^{55}$ETIL |

FIGURE 2

| | | | | |
|---|---|---|---|---|
| *E.coli LT* | KMWADSRPPD | LYDHARGTQ | YDDGVVSTSLSLRSA | SPHPYEQEVSALGGI |
| *N.meningitidis* | FLVRGLSCQQD | VYAHQIETG | YDGQYISTTIDKELA | PENPYEKEVTIRAED |
| *S.coelicolor* | TLMRSDSRGPPD | VVFEEGFHAKDVQNGQYDVEKYVLVNQPSPMVSTSVDHDLM | HKWADQVEVAFPGGI |
| *M.pneumoniae* | FVARVDERSPE | FFEHILSTN | GRSNFISTSFFDTAA | TSFAWQREWFDGPI |
| *S.typhi* | TVVRVDSTPPD | | SCSQGSSDSRVTATT | TMMRLQREVVSTLSI |
| *S.paratyphi* | TVVRVDSTPPD | | SCSQGSSDSRVTATT | TMMRLQREVVSTLSI |
| *S.pyogenes* | VVTRVAIETFL | | TKHSFMSTTALKNGA | SAVPSEVFLLFPRGC |

ADP-RIBOSYLATING BACTERIAL TOXINS

CROSS-REFERENCE TO RELATED APPLICATIONS

This application is a 35 U.S.C. §371 filing of PCT/IB02/02080, filed Mar. 28, 2002, which in turn claims the benefit of Great Britain application 0108024.1, filed Mar. 30, 2001 from which priority is claimed under 35 U.S.C. §120, and which applications are all incorporated herein by reference in their entireties.

All documents cited herein are incorporated by reference in their entirety.

TECHNICAL FIELD

This invention is in the field of ADP-ribosylating bacterial toxins and their uses.

BACKGROUND ART

ADP-ribosylating bacterial exotoxins are widely known. Examples include diphtheria toxin (*Corynebacterium diphtheriae*), exotoxin A (*Pseudomonas aeruginosa*), cholera toxin (CT; *Vibrio cholerae*), heat-labile enterotoxin (LT; *E. coli*) and pertussis toxin (PT).

The toxins catalyse the transfer of an ADP-ribose unit from $NAD^+$ to a target protein. CT, for instance, transfers ADP-ribose to a specific arginine side chain of the α subunit of $G_S$, which blocks the ability of $G_S$ to hydrolyse GTP to GDP. This locks the protein in its 'active' form, so adenylate cyclase activity is permanently activated. Cellullar cAMP levels rise, leading to the active transport of ions from the cell and the loss of water into the gut [1].

The toxins are typically divided into two functionally distinct domains—A and B. The A subunit is responsible for the toxic enzymatic activity, whereas the B subunit is responsible for cellular binding. The subunits might be domains on the same polypeptide chain, or might be separate polypeptide chains. The subunits may themselves be oligomers e.g. the A subunit of CT consists of $A_1$ and $A_2$ which are linked by a disulphide bond, and its B subunit is a homopentamer. Typically, initial contact with a target cell is mediated by the B subunit and then subunit A alone enters the cell.

Crystal structures [2] are known for LT [3], CT [4] and PT [5].

The toxins are typically immunogenic, and have been proposed for use in acellular vaccines. One problem, however, is that the proteins retain their toxic activity in the vaccines. To avoid this problem, site-directed mutagenesis of key active site residues has been used to remove toxic enzymatic activity whilst retaining immunogenicity [e.g. refs. 6 (CT and LT), 7 (PT), 8 etc.]. Current acellular whooping cough vaccines include a form of pertussis toxin with two amino acid substitutions ($Arg^9 \rightarrow Lys$ and $Glu^{129} \rightarrow Gly$; 'PT-9K/129G' [9]).

As well as their immunogenic properties, the toxins have been used as adjuvants. Parenteral adjuvanticity was first observed in 1972 [10] and mucosal adjuvanticity in 1984 [11]. It was surprisingly found in 1993 that the detoxified forms of the toxins retain adjuvanticity [12].

It is an object of the invention to provide further ADP-ribosylating bacterial toxins.

DISCLOSURE OF THE INVENTION

The amino acid sequences of six different ADP-ribosylating toxins from Gram positive and Gram negative bacteria are given in SEQ IDs 1, 3, 4, 5, 6 and 7. These toxins are from *Neisseria meningitidis, Streptomyces coelicolor, Mycoplasma pneumoniae, Salmonella typhimurium, Salmonella paratyphi,* and *Streptococcus pyogenes*. The existence of ADP-ribosylating toxins in these bacterial species has not previously been suggested and, furthermore, there is only a low level of sequence identity between these toxins and toxins such as CT, LT and PT.

Toxins of the Invention

The invention provides a protein having an amino acid sequence consisting of one of SEQ IDs 1, 3, 4, 5, 6 and 7. These proteins are referred to hereafter as "toxins of the invention".

Mutant Toxins of the Invention

The invention also provides a protein having an amino acid sequence consisting of one of SEQ IDs 1, 3, 4, 5, 6 and 7, except that the amino acid sequence contains one or more mutations. The mutation(s) preferably reduce or eliminate the ADP-ribosylating activity of the protein.

The mutations may each independently be a substitution, an insertion, or a deletion. Preferably, the amino acid sequences contains fewer than twenty mutations (e.g. 19, 18, 17, 16, 15, 14, 13, 12, 11, 10, 9, 8, 7, 6, 5, 4, 3, 2 or 1). Each mutation preferably involves a single amino acid.

Preferred mutations are single amino acid substitutions (e.g. SEQ IDs 10, 12, 14 & 16).

The invention also provides a process for diminishing the ADP-ribosylating enzymatic activity of a toxin of the invention, comprising mutating one or more amino acid residues of said toxin. This may conveniently be achieved by performing site-directed mutagenesis on nucleic acid encoding the toxin. The invention further provides a protein obtainable by this process.

Mutations may also be introduced to improve stability e.g. the insertion of disulphide bonds [13].

The proteins defined above are referred to hereafter as "mutant toxins of the invention" or "toxoids of the invention".

Preferred sites for mutation are given in Table 1, together with preferred mutations at those sites.

Proteins of the Invention

The invention provides a protein comprising the amino acid sequence of a toxin or mutant toxin of the invention.

It also provides a protein comprising an amino acid sequence having sequence identity to the amino acid sequence of a toxin or mutant toxin of the invention. The degree of sequence identity is preferably greater than 50% (e.g. 60%, 70%, 80%, 90%, 95%, 99% or more). These proteins include homologs, orthologs, allelic variants and functional mutants. Typically, 50% identity or more between two proteins is considered to be an indication of functional equivalence. Identity between proteins is preferably determined by the Smith-Waterman homology search algorithm as implemented in the MPSRCH program (Oxford Molecular), using an affine gap search with parameters gap open penalty=12 and gap extension penalty=1.

The invention further provides a protein comprising a fragment of a toxin or mutant toxin of the invention. The fragment should comprise at least n consecutive amino acids from the toxin or mutant toxin and, depending on the particular sequence, n is 7 or more (e.g. 8, 10, 12, 14, 16, 18, 20, 30, 40, 50, 60, 70, 80, 90, 100 or more). Preferably the fragment comprises one or more epitopes from the toxin. Preferred fragments are those common to two or more of SEQ ID 1, 3, 4, 5, 6 and 7.

The toxins, mutant toxins and proteins defined above are collectively referred to hereafter as the "proteins of the invention".

The proteins of the invention can, of course, be prepared by various means (e.g. recombinant expression, purification from native host, chemical synthesis etc.) and in various forms (e.g. native, fusions etc.). They are preferably prepared in substantially pure form (i.e. substantially free from host cell proteins).

The invention also provides the proteins of the invention (particularly the mutant toxins) for use as adjuvants and, in particular, as mucosal adjuvants.

The invention also provides the use of proteins of the invention in the manufacture of a medicament for raising an immune response in an animal. The medicament is preferably an immunogenic compositions (e.g. a vaccine), and will comprise, in addition to a protein of the invention, an antigen against which an immune response is to be raised. The medicament is preferably administered mucosally e.g. orally or intranasally.

The invention also provides immunogenic compositions (e.g. a vaccine) comprising a protein of the invention in admixture with a second antigen. It also provides a kit comprising a protein of the invention and a second antigen for simultaneous, separate or sequential administration. The second antigen is preferably one of the *N. meningitidis* proteins disclosed in references 14 to 20. The composition may comprise a third antigen, a fourth antigen, a fifth antigen etc., one or more of which may be selected from the *N. meningitidis* proteins disclosed in these seven references.

According to a further aspect, the invention provides antibody which binds to a protein of the invention. These may be polyclonal or monoclonal and may be produced by any suitable means. The antibody may include a detectable label.

According to a further aspect, the invention provides nucleic acid encoding the proteins of the invention. Nucleic acid comprising a fragment of these coding sequences are also provided. These should comprise at least n consecutive nucleotides from the coding sequence and, depending on the particular sequence, n is 10 or more (e.g. 12, 14, 15, 18, 20, 25, 30, 35, 40, 50, 60, 70, 80, 90, 100, 150, 200 or more). These can be used in hybridisation reactions (e.g. Northern or Southern blots, or in nucleic acid microarrays or 'gene chips') and amplification reactions (e.g. PCR, SDA, SSSR, LCR, NASBA, TMA) etc.

The invention also provides nucleic acid comprising one or more of SEQ IDs 2, 8, 11, 13, 15, 17, 18, 19, 20, 21, 22, 23, 24, 25 and/or 26.

It should also be appreciated that the invention provides nucleic acid comprising sequences complementary to those described above (e.g. for antisense or probing, or for use as primers).

Nucleic acid according to the invention can, of course, be prepared in many ways (e.g. by chemical synthesis, from genomic or cDNA libraries, from the organism itself etc.) and can take various forms (e.g. single stranded, double stranded, vectors, primers, probes etc.).

Nucleic acid according to the invention may be labelled e.g. with a radioactive or fluorescent label. This is particularly useful where the nucleic acid is to be used as a primer or probe e.g. in PCR, LCR or TMA.

In addition, the term "nucleic acid" includes DNA and RNA, and also their analogues, such as those containing modified backbones, and also peptide nucleic acids (PNA) etc.

According to a further aspect, the invention provides vectors comprising nucleic acid of the invention (e.g. cloning or expression vectors) and host cells transformed with such vectors.

According to a further aspect, the invention provides compositions comprising protein, antibody, and/or nucleic acid according to the invention. These compositions may be suitable as immunogenic compositions, for instance, or as diagnostic reagents, or as vaccines.

The invention also provides nucleic acid, protein, or antibody according to the invention for use as medicaments (e.g. vaccines) or diagnostic reagents. It also provides the use of nucleic acid, protein, or antibody of the invention in the manufacture of: (i) a medicament for treating or preventing bacterial infection; (ii) a diagnostic reagent for detecting the presence of bacteria or of antibodies raised against bacteria; and/or (iii) a reagent which can raise antibodies against bacteria. Said bacteria are preferably *Neisseria meningitidis, Streptomyces coelicolor, Mycoplasma pneumoniae, Salmonella typhimurium, Salmonella paratyphi,* or *Streptococcus pyogenes.*

The invention also provides a method of treating a patient, comprising administering a therapeutically effective amount of nucleic acid, protein, and/or antibody of the invention.

The invention also provides a kit comprising primers (e.g. PCR primers) for amplifying a target sequence contained within a bacterium nucleic acid sequence, the kit comprising a first primer and a second primer, wherein the first primer is substantially complementary to said target sequence and the second primer is substantially complementary to a complement of said target sequence, wherein the parts of said primers which have substantial complementarity define the termini of the target sequence to be amplified.

According to further aspects, the invention provides various processes.

A process for producing a protein of the invention is provided, comprising the step of culturing a host cell of to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridising conditions to form duplexes; and (b) detecting said duplexes.

A process for detecting bacteria in a biological sample is also provided, comprising the step of contacting nucleic according to the invention with the biological sample under hybridising conditions. The process may involve nucleic acid amplification (e.g. PCR, SDA, SSSR, LCR, TMA etc.) or hybridisation (e.g. microarrays, blots, hybridisation with probe in solution etc.).

A process for detecting a protein of the invention is provided, comprising the steps of: (a) contacting an antibody of the invention with a biological sample under conditions suitable for the formation of an antibody-antigen complexes; and (b) detecting said complexes.

A summary of standard techniques and procedures which may be employed to perform the invention (e.g. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Third Edition* (2001); *DNA Cloning, Volumes I and II* (D. N Glover ed. 1985); *Oligo-* nucleotide Synthesis (M. J. Gait ed, 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Mayer and Walker, eds. (1987), Immunochemical Methods in Cell and Molecular Biology (Academic Press, London); Scopes, (1987) Protein Purification: Principles and Practice, Second Edition (Springer-Verlag, N.Y.), and Handbook of Experimental Immunology, Volumes I-IV (D. M. Weir and C. C. Blackwell eds 1986).

Standard abbreviations for nucleotides and amino acids are used in this specification.

Definitions

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g. a composition "comprising" X may consist exclusively of X or may include something additional e.g. X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a *staphylococcus* sequence is heterologous to a mouse host cell. A further example would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (eg. see U.S. Pat. No. 5,753,235).

Expression Systems

Nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating downstream (3') transcription of a coding sequence (eg. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100-200 bp upstream of the TATA box. An upstream promoter element determines the rate at which transcription is initiated and can act in either orientation [Sambrook et al.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes (e.g., the murine metallotheionein gene) also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, as they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *PNAS USA* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot & Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminator/polyadenylation signals include those derived from SV40 [Sambrook et al].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers & Smith, *Texas Agricultural Experiment Station Bulletin No. 1555* (1987) (hereinafter "Summers & Smith").

Prior to inserting the DNA sequence encoding the protein into the baculovirus genome, the above described components, comprising a promoter, leader (if desired), coding sequence, and transcription termination sequence, are usually assembled into an intermediate transplacement construct (transfer vector). This may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extra-chromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. M any other vectors, known to those of skill in the art, have also been designed. These include, for example, pVL985 (which alters the polyhedrin start codon from ATG to ATT, and which introduces a BamHI cloning site 32 bp downstream from the ATT; see Luckow & Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late limes in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l. Acad. Sci. USA*, 82:8404; mouse IL-3, (Miyajima et al., (1987) *Gene* 58:273; and human glucocerebrosidase, Martin et al. (1988) *DNA*, 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers & Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91 The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers & Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoprera frugiperda*, and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg. Summers & Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, etc. As appropriate, the product may be further purified, as required, so as to remove substantially any insect proteins which are also present in the medium, so as to provide a product which is at least substantially free of host debris, eg. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in Jones & MacMillin, pages 21-52 of *Advanced Plant Physiology, Malcolm B. Wilkins, ed.*, 1984 Pitman Publishing Limited. References that describe other metabolically-regulated genes: Sheen, *Plant Cell,* 2:1027-1038(1990); Maas et al., *EMBO J.* 9:3447-3452 (1990); Benkel & Hickey, *PNAS USA.* 84:1337-1339 (1987).

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a cell has been transformed. A general review of suitable markers, for example for the members of the grass family, is found in Wilmink & Dons, 1993, *Plant Mol. Biol. Repir,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed & Maniatis, *Cell* 41:95-105, 1985.

The vector can be microinjected directly into plant cells by use of micropipettes to mechanically transfer the recombinant DNA. Crossway, *Mol. Gen. Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *PNAS USA,* 79, 1859-1863, 1982.

The vector may also be introduced into the plant cells by electroporation. (Fromm et al., *PNAS USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihol, Daucus, Arabidopsis, Brassica, Raphanus, Sinapis, Atropa, Capsicum, Darura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Petargonium, Panicum, Pennisetum, Ranunculus, Senecio, Salpiglossis, Cucumis, Browaalia, Glycine, Lolium, Zea, Triticum, Sorghum,* and *Datura.*

Means for regeneration vary between plant species, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glulamic acid and proline to the medium, especially for such species as corn and alfalfa. Shoots and roots normally develop simultaneously. Efficient regeneration will depend on the medium, on genotype, and on the history of the culture. If these three variables are controlled then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) Nature 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-01217751. The g-laotamase (bla) promoter system (Weissmann (1981) "The cloning of interferon and other mistakes." In *Interferon* 3 (ed. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the rac promoter is a hybrid trp-lac promoter comprised of both trp promoter and lac operon sequences that is regulated by the lac repressor [Amann et al. (1983) *Gene* 25:167; de Boer et al. (1983) *PNAS USA* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *PNAS USA* 82:1074]. In addition, a hybrid promoter can also be comprised of a bacteriophage promoter and an *E. coli* operator region (EP-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *PNAS USA* 82:7212]. As an additional example, the signal sequence of the alpha-amylase gene from various *Bacillus* strains can be used to secrete heterologous proteins from *B. subtilis* [Palva et al. (1982) *PNAS USA* 79:5582; EP-A-0 244 0421.

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryolic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbial.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *PNAS USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbial.* 54:655]; *Streptococcus lividans* [Powell et al. (1988) *Appl. Environ. Microbial.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbial. Lett.* 60:273; Palva et al. (1982) *PNAS USA* 79:5582; EP-A-0 036 259 and EP-A-0 063 953; WO 84/04541, *Bacillus*], [Miller et al. (1988) *PNAS USA*. 85:856; Wang et al. (1990) *J. Bacteriol.* 172:949, *Campylobacter*], (Cohen et al. (1973) *PNAS USA* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. Boyer & Nicosia); Mandel et al. (1970) *J. Mol. Biol.* 53:159; Taketo (1988) *Biochim. Biophys. Acia* 949:318; *Escherichia*], [Chassy et al. (1987) *FEMS Microbial. Lett.* 44:173 *Lactobacillus*]; [Fiedler et al. (1988) *Anal. Biochem* 170:38, *Pseudomonas*]; [Augustin et al. (1990) *FEMS Microbial. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbial.* 54:655; Somkuti et al. (1987) *Proc. 4th Evr. Cong. Biotechnology* 1:412, Streplococcus].

v. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, so sequences encoding enzymes in the metabolic pathway provide particularly useful promoter sequences. Examples include alcohol dehydrogenase (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *PNAS USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PH05 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *PNAS USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. DNA encoding suitable signal sequences can be derived from genes for secreted yeast proteins, such as the yeast invertase (EP-A-0012873; JPO 62,096,086) and A-factor (U.S. Pat. No. 4,588,684) genes. Alternatively, leaders of non-yeast origin, such as an interferon leader, exist that also provide for secretion in yeast (EP-A-0060057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17-24], pC1/1 [Brake et al. (1984) *PNAS USA* 81:4642-4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually ~10 to ~150. A host containing a high copy number plasmid will preferably have at least about 10, and more preferably at least ~20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector, See Orr-Weaver et al., supra. One or more expression construct may integrate, possibly affecting levels of recombinant protein produced [Rine et al. (1983) *PNAS USA* 80:6750]. The chromosomal sequences included in the vector can occur either as a single segment in the vector, which results in the integration of the entire vector, or two segments homologous to adjacent segments in the chromosome and flanking the expression construct in the vector; which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbial, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141], *Hansenula polymorpha* [Gleeson, et al. (1986) *J. Gen. Microbial.* 132:3459; Roggenkamp et al. (1986) *Mol. Gen. Genet.* 202:302], *Kluyveromyces fragilis* [Das, et al. (1984) *J. Bacterial.* 158:1165], *Kluyveromyces lactis* [De Louvencourt et al. (1983) *J. Bacterial.* 154:737; Van den Berg et al. (1990) *Bio/Technology* 8:135], *Pichia guillerimondii* [Kunie et al. (1985) *J. Basic Microbial.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *PNAS USA* 75:1929; Ito et al. (1983) *J. Bacterial.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbial.* 25:141; *Candida*]; [Gleeson et al. (1986) *J. Gen. Microbial.* 132:3459; Roggenkamp et al. (1986) *Mol. Gen. Genet.* 202:302; *Hansenula*]; [Das et al. (1984) *J. Bacterial.* 158:1165; De Louvencourt et al. (1983) *J. Bacterial.* 154:1165; Van den Berg et al. (1990) *Bio/Technology* 8:135; *Kluyveromyces*]; [Cregg er al. (1985) *Mol. Cell. Biol.* 5:3376; Kunze et al. (1985) *J. Basic Microbial.* 25:141; U.S. Pat. Nos. 4,837,148 and 4,929,555; *Pichia*]; [Hinnen et al. (1978) *PNAS USA* 75; 1929; Ito et al. (1983) *J. Bacterial.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying proteins of the invention.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goal antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with mycloma cells to form hybridomas, and are cultured in a selective medium (eg. hypoxanthine, aminopterin, thymidine medium, "HAT"). The resulting hybridomas are plated by limiting dilution, and are assayed for production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon their size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines according to the invention may either be prophylactic (ie. to prevent infection) or therapeutic (ie. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12 etc.), interferons (eg. γ interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acelyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (eg. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, their taxonomic group (eg. non-human primate, primate, etc.), the capacity of their immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection, either subcutaneously, intramuscularly, or transdermally/transcutaneously (eg. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be used [eg. Robinson & Torres (1997) *Seminars in Immunol* 9:271-283; Donnelly et al. (1997) *Annu Rev Immunol* 15:617-648].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of coding sequence can be induced using endogenous mammalian or heterologous promoters. Expression of coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:51-64; Kimura (1994) *Human Gene Therapy* 5:845-852; Connelly (1995) *Human Gene Therapy* 6:185-193; and Kaplitt (1994) *Nature Generics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses eg. MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) J Virol 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Manassas, Va. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *PNAS USA* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (ie. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary HSV vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC with accession numbers VR-977 and VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Manassas, Va. or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem L*401; pox viruses such as canary pox virus or vaccinia virus, for example ATCC VR-111 and ATCC VR-2010 and those described in Fisher-Hoch (1989) *PNAS USA* 86:317; Flexner (1989) *Ann NY Acad Sci* 569:86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *PNAS USA* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and Nature (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR; 1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eukaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *PNAS USA* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, prolamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocylosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, prolamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquilously-active promoters. Further non-viral delivery suitable for use includes mechanical delivery systems such as the approach described in Woffendin et al (1994) *PNAS USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *PNAS USA* 84:7851; Plant (1989) *Anal Biochem* 176: 420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, polynucleotide compositions of the invention can be administered (1) directly to the subject; (2) delivered ex vivo, to cells derived from the subject; or (3) in vitro for expression of recombinant proteins. Subjects to be treated can be birds or mammals (including humans).

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hemalopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene-mediated transfection, protoplasm fusion, electroporation, encapsulation of polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, Etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acia.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *PNAS USA* 84:7413-7416); mRNA (Malone (1989) *PNAS USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *PNAS USA* 75:4194-4198;

WO90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl elhanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512-527; Szoka (1978) *PNAS USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *PNAS USA* 76:3348); Enoch & Strittmatter (1979) *PNAS USA* 76:145; Fraley (1980) *J. Biol. Chem.* (1980) 255: 10431; Szoka & Papahadjopoulos (1978) *PNAS USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C & E, over time these lipoproteins lose A and acquire C & E. VLDL comprises A, B, C & E apoproteins, LDL comprises apoprotein B; and HDL comprises apoproteins A, C, & E.

The amino acid of these apoproteins are known and are described in, for example, Breslow (1985) Annu Rev. Biochem 54:699; Law (1986) Adv. Exp Med. Biol. 151:162; Chen (1986) J Biol Chem 261:12918; Kane (1980) *PNAS USA* 77:2465; and Utermann (1984) Hum Genet 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem*, 15:403 and Radding (1958) *Biochim Biophys Acta* 30: 443. Lipoproteins can also be purchased from commercial suppliers, such as Biomedical Techniologies, Inc., Stoughton, Mass., USA. Further description of lipoproteins can be found in WO98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

Proteins of the invention can be used in immunoassays to detect antibody levels (or, conversely, antibodies of the invention can be used to detect protein levels). Immunoassays based on well defined, recombinant antigens can be developed to replace invasive diagnostics methods. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57, "Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%(G+C)]-0.6(\% \text{ formamide})-600/n-1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of hybridization increases (ie. stringency), it becomes less likely for hybridization to occur between strands that are non-homologous, and as a result, background decreases. If a radiolabeled probe is not completely homologous with the immobilized fragment (as is frequently the case in gene family and interspecies hybridization experiments), the hybridization temperature must be reduced, and background will increase. The temperature of washes affects the intensity of the hybridizing band and the degree of background in a similar way. The stringency of washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex that is stable enough to be detected Nucleic acid probes will hybridize to the nucleic acid of the invention (sense and/or antisense strands). Though many different nucleotide sequences will encode the amino acid sequence, the wild-type sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to a sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional sequence may also be helpful as a label to detect the formed duplex. For example, a non-complementary nucleotide sequence may be attached to the 5' end of the probe, with the remainder of the probe sequence being complementary to a bacterial sequence. Alternatively, non-complementary bases or longer sequences can be interspersed into the probe, provided that the probe sequence has sufficient complementarity with the a bacterial sequence in order to hybridize therewith and thereby form a duplex which can be detected.

The exact length and sequence of the probe will depend on the hybridization conditions (e.g. temperature, salt condition etc.). For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*PNAS USA* (1983) 80: 7461], or using commercially available automated oligonucleotide synthesizers.

The chemical nature of the probe can be selected according to preference. For certain applications, DNA or RNA are appropriate. For other applications, modifications may be incorporated eg. backbone modifications, such as phosphorothioates or methylphosphonates, can be used to increase in vivo half-life, alter RNA affinity, increase nuclease resistance etc. [eg. Agrawal & Iyer (1995) *Curr. Opin. Biotechnol* 6:12-19; Agrawal (1996) *TIBTECH* 14:376-3871; analogues such as PNAs may also be used [eg. see Corey (1997) *TIBTECH* 15:224-229; Buchardt e al. (1993) *TIBTECH* 11:384-386].

Alternatively, the polymerase chain reaction (PCR) is another well-known means for detecting small amounts of target nucleic acid. The assay is described in Mullis et al. [*Meth. Enzymol.* (1987) 155:335-350] & U.S. Pat. Nos. 4,683,195 & 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired bacterial sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the bacterial sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

BRIEF DESCRIPTION OF DRAWINGS

FIG. 1 shows an alignment of catalytic domains of various bacterial toxins, including the *N. meningitidis* toxin of the invention (NMB1343). Residues important for catalytic activity are shown enlarged.

FIG. 2 shows a multiple sequence alignment of conserved regions of LT and toxins of the invention. Residues important for catalytic activity are underlined. Residues important for the conservation of structure have a shaded background. Other conserved residues are indicated in bold.

MODES FOR CARRYING OUT THE INVENTION

Figure 3B:
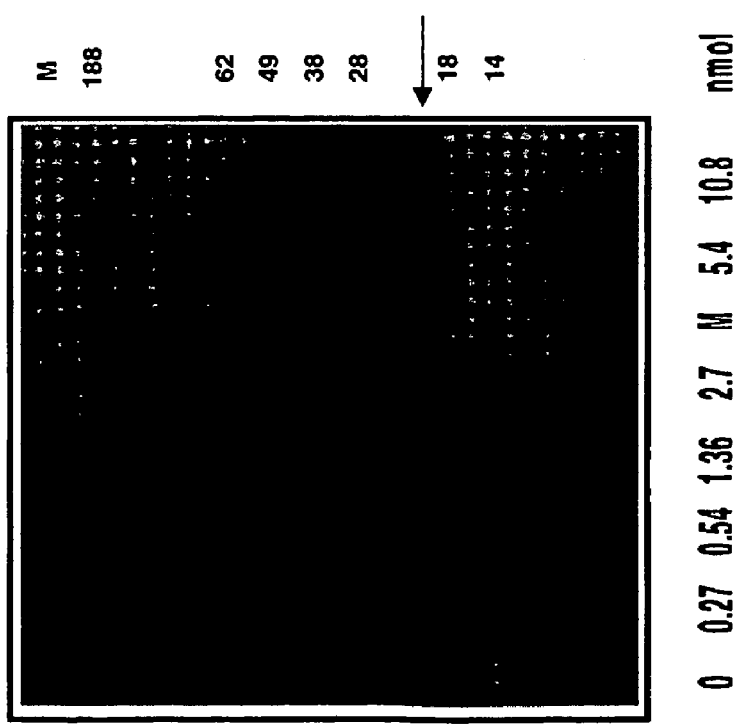
In FIG. 3B, the lanes are: (L1) 95° C.; (L2) Novobiocin, 5 mMol; (L3) GTP, 10 mMol; (L4) ATP, 10 mMol; (L5) ADP-ribose, 10 mmol; (L6) Nicotinamide (NAM), 10 mMol; (L7) control. The arrow shows the position of the toxin.

Toxin Gene from *Neisseria meningitidis*, Serogroup B

A protein with amino acid sequence <SEQ ID 1> was identified in *N. meningitidis* (serogroup B, strain MC58). This is encoded by a gene having nucleotide sequence <SEQ ID 2>.

The protein ('NMB1343') shows 27% identity to CT-A [CAA41592] over 127aa overlap:

```
1343            MGNFLYRGISCQQDE-QNNGQLKPKGNKAEVAIRYDGKFKYDGKATHGPSVKNAV
                |||:  |    ||  :::|  |  |:|::        :|       :|  :::  :
CT-A   MVKIIFVFFIFLSSFSYANDDKLYRADSRPPDEIKQSGGLMPRGQS-----EY-----FD----RGTQMNINL
1343   YAHQ--IETGL--YDGCYISTTTDKEIAKKFATS--SGIENGYIYVLNR---DLFGQYSIFEYEVEHPENPNEK
       |  |    :||:  :|   |:||:  : :  |:     :  ||   :  ||||:       ::|:   :::    ||:    |:
CT-A   YDHARGTQTGFVRHDDGYVSTSISLRSAHLVGQTILSGHSTYYIYVIATAPNMFNVNDVLGAYSPHPD---EQ
1343   EVTIRAEDCGCIPEEVIIAKELIEIN* (SEQ ID NO: 1)
       ||:
CT-A   EVSALGGIPYSQIYGWYRVHFGVLDEQLHRNRGYRDRYYSNLDIAPAADGYGLAGFPPEHRAWREEPWIHHAP
CT-A   PGCGNAPRSSMSNTCDEKTQSLGVKFLDEYQSKVKRQIFSGYQSDIDTHNRIKDEL (SEQ ID NO: 27)
```

The protein shows 30% identity to LT-A [P06717] over 125aa overlap:

```
1343            MGNFLYRGISCQQDE-QNNGQLKPKGNKAEVAIRYDGKFKYDGKATHGPSVKNAV
                |:  |||:  |     ||  :  :|  |  |  |:|::          :|        :|  :::    :
LT-A   MKNITFIFFILLASPLYANGDRLYRADSRPPDEIKRSGGLMPRGHNE----YFD----------RGTQMNINL
1343   YAHQ--IETGL--YDGCYISTTTDKEIAKKFATS--SGIENGYIYVLNR--------DLFGQYSIFEYEVEHP
       |  |    :||:   ||   |:||:  : :  |:     :  ||    :  ||||:                 |::|  ||  :  ||  |
LT-A   YDHARGTQTGFVRYDDGYVSTSLSLRSAHLAGQSILSGYSTYYIYVIATAPNMFNVNDVLGVYSPHPYEQEVS
1343   ENPNEKEVTIRAEDCGCIPEEVIIAKELIEIN* (SEQ ID NO: 1)

LT-A   ALGGIPYSQIYGWYRVNFGVIADERLHRNREYRDRYYRNLNIAPAEDGYRLAGFPPDHQAWREEPWIHHAPQG
LT-A   CGNSSRTITGDTCNEETQNLSTIYLREYQSKVKRQIFSDYQSEVDIYNRIRDEL258 (SEQ ID NO: 28)
```

The *N. meningitidis* protein therefore shows only a low level of identity with these toxins. Indeed, a GRASTA search of the *N. meningitidis* genome using the CT-A or LT-A sequences does not identify this protein in the top 50 hits. Similarly, the protein itself is annotated simply as 'hypothetical protein'. Whilst ADP ribosyltransferase activity is not suggested for this protein by algorithmic methods, more detailed analysis of the sequence alignment in the regions of key catalytic residues reveals good conservation (FIG. 1).

No corresponding gene was identified in *N. meningitidis* serogroup A (strain Z2491 [21]) or in *N. gonorrhoaeae*.

Toxin Gene from *Streptomyces coelicolor* A3(2)

A protein with amino acid sequence <SEQ ID 3> (CAB76015) was identified in *S. coelicolor*:

```
  1  MITTSLRRRT AAAVLSLSAV LATTAATAPG AAPAPSAAPA KAAPACPQFD DRTKAAADRG

61  VDVDRITPEP VWRTTCGTLY RSDSRGPQVV FEEGFHAKDV QNGQYDVEKY VLVNQPSPYV

121  STSYDHDLYK TWYKSGYNYY VDAPGGIDVN KTIGDTHKWA DQVEVAFPGG IQRKYIIGVC

181  PVDRQTKTEI MSDCESNPHY QPWH
```

This protein shows 27% identity to CT-A over 136aa overlap:

```
SEQID3    PACPQFDDRTKAAADRGVDVDRITPEPVWRTTCGTLYRSDSRGPQVV------------
             : :                        |||:|||  |    :
ct.pep            MVKIIFVFFIFLSSFSYANDDKLYRADSRPPDEIKQSGGLMPRGQS
SEQID3    ----------FEEGFHAKDVQNGQYDVEKYVLVNQPSPYVSTSYD----HDLYKTWYKSG
                    || |: ::    ||:  :|:|          :|  :  ||||    |   :|
ct.pep    EYFDRGTQMNINLYDHARGTQTG--------FVRHDDGYVSTSISLRSAHLVGQTILSGH
SEQID3    YNYYV----DAPGGIDVNKTIGDTHKWADQVEVAFPGGIQRKYIIGVCPVDRQTKTEIMS
            :||:      ||: ::||  ::|         |: ||:  ||| :  | |    |
ct.pep    STYYIYVIATAPNMFNVNDVLGAYSPHPDEQEVSALGGIPYSQIYGWYRVHFGVLDEQLH
SEQID3    DCESNPHYQPWH (SEQ ID NO: 3)

ct.pep    RNRGYRDRYYSNLDIAPAADGYGLAGFPPEHRAWREEPWIHHAPPGCGNAPRSSMSNTCD (SEQ ID NO: 27)
```

As for *N. meningitidis*, therefore, there is only a low level of overall identity with known toxins, but key catalytic residues are conserved. The database annotation of 'putative secreted protein' does not suggest ADP ribosyltransferase activity.

Toxin Gene from *Mycoplasma pneumoniae* M129 [22]

A protein with amino acid sequence <SEQ ID 4> [P75409] was identified in *M. pneumoniae*:

```
  1  MPNPVRFVYR VDLRSPEEIF EHGFSTLGDV RNFFEHILST NFGRSYFIST SETPTAAIRF

61  FGSWLREYVP EHPRRAYLYE IRADQHFYNA RATGENLLDL MRQRQVVFDS GDREMAQMGI

121  RALRTSFAYQ REWFTDGPIA AANVRSAWLV DAVPVEPGHA HHPAGRVVET TRINEPEMHN

181  PHYQELQTQA NDQPWLPTPG IATPVHLSIP QAASVADVSE GTSASLSFAC PDWSPPSSNG

241  ENPLDKCIAE KIDNYNLQSL PQYASSVKEL EDTPVYLRGI KTQKTFMLQA DPQNNNVFLV

301  EVNPKQKSSF PQTIFFWDVY QRICLKDLTG AQISLSLTAF TTQYAGQLKV HLSVSAVNAV

361  NQKWKMTPQD IAITQFRVSS ELLGQTENGL FWNTKSGGSQ HDLYVCPLKN PPSDLEELQI

421  IVDECTTHAQ FVTMRAASTF FVDVQLGWYW RGYYYTPQLS GWSYQMKTPD GQIFYDLKTS

481  KIFFVQDNQN VFFLHNKLNK QTGYSWDWVE WLKHDMNEDK DENFKWYFSR DDLTIPSVEG

541  LNFRHIRCYA DNQQLKVIIS GSRWGGWYST YDKVESNVED KILVKDGFDR F
```

This protein shows 29% identity to PT over 243aa overlap:

```
seqid4                         MPNPVRFVYRVDLRSPEEIFEHGFSTLGDVRN
                                :|   ||| |  || |  ||::|::||::  |
pt.pep    AIRQTARTGWLTWLAILAVTAPVTSPAWADDPPATVYRYDSRPPEDVFQNGFTAWGNNDN
seqid4    FFEHIL--STNFGRSY--FISTSETPTAAIRFFGSWLREYVP-EHPRRA------YLYEI
          ::|:    |  :  |   |:|||    |  ::   ::|   |:|       |:||:
pt.pep    VLDHLTGRSCQVGSSNSAFVSTSSSRRYTEVYLEHRMQEAVEAERAGRGTGHFIGYIYEV
```

```
seqid4    RADQHFYNARATGENLLDLMRQRQVVFDSGDREMAQMGIRALRTSFAYQREWFTDGPIAA
          |||::||:|  ::   : |    :    : |       ||  |   ||  |::: |
pt.pep    RADNNFYGAASSYFEYVDTYG------DNAGRILAG----ALAT---YQSEYLAHRRIPP seqid4    ANVRSAWLVDAVPVEPGHAHHPAGRVVETTRINEPEMHNPHYQELQTQANDQPWLPTPGI
          |:|  :  |          :|   |  : |||     |:  :|   ||:|| :|:    ::
pt.pep    ENIRRVTRV---------YH-NGITGETTTT---EYSNARYVSQQTRANPNPYTSRRSV seqid4    ATPVHLSIPQAASVADVSEGTSASLSFACPDWSPPSSNGENPLDKCIAEKIDNYNLQSLP
          |:  |   ::  :  | |     :    ::|  | |    ||
pt.pep        ASIVG-TLVRMAPVIGACMARQAESSEAMAAWSERAGEAMVLVYYESIAYSF (SEQ ID NO: 29)

seqid4    QYASSVKELEDTPVYLRGIKTQKTFMLQADPQNNNVFLVEVNPKQKSSFPQTIFFWDVYQ
```

As for *N. meningitidis* and *S. coelicolor*, therefore, there is only a low level of overall identity with a known toxin, but key catalytic residues are conserved. The database annotation of 'hypothetical protein' does not suggest ADP ribosyltransferase activity.

Toxin Gene from *Salmonella typhimurium* L72 (Strain SGSC1412)

A protein with the amino acid sequence <SEQ ID 5> was identified in *S. typhimurium*:

```
  1    MKKLIFLTLS IVSFNNYAVD FVYRVDSTPP DVIFRDGFSL LGYNRNFQQF

51    ISGRSCSGGS SDSRYIATTS SVNQTYAIAR AYYSRSTFKG NLYRYQIRAD

101    NNFYSLLPSI TYLETQGGHF NAYEKTMMRL QREYVSTLSI LPENIQKAVA

151    LVYDSATGLV KDGVSTMNAS YLGLSTTSNP GVIPFLPEPQ TYTQQRIXAF

201    GPLISSCFSI GSVCHSHRGQ RADVYNMSFY DARPVIELIL SK
```

This protein shows 29% identity to PT over 232aa overlap:

```
SEQID5            MKKLIFLTLSIVSFNNYAVDFVYRVDSTPPDVIFRDGFSLLGYNRNFQQFI
                                             ||| || ||: :|::||:  | | |  : :
pt.pep   ARTGWLTWLAILAVTAPVTSPAWADDPPATVYRYDSRPPEDVFQNGFTAWGNNDNVLDHL
                  20        30        40        50        60        70

SEQID5   SGRSCSGGSSDSRYIATTSS-----------VNQTYAIARAYYSRSTFKGNLYRYQIRAD
         :||||: |||:| :::|:||           ::::     ||   : :  | |  | |:|||
pt.pep   TGRSCQVGSSNSAFVSTSSSRRYTEVYLEHRMQEAVEAERAGRGTGHFIG--YIYEVRAD SEQID5   NNFYSLLPS-ITYLETQGGHFN-AYEKTMMRLQREYVSTLSILPENIQKAVALVYDSATG
         ||||:    | : |::| | : :      ::    | ||::    : ||||:::: : ::: ||
pt.pep   NNFYGAASSYFEYVDTYGDNAGRILAGALATYQSEYLAHRRIPPENIRRVTRVYHNGITG SEQID5   LVKDGVSTMNASYLGLSTTSNPGVIPFLPEPQTYTQQRIXAFGPLISSCFSIGSVCHSHR
          :      : || |:: :| :||:         | |   ::       | |:       ||: | :::
pt.pep   ETTTTEYS-NARYVSQQTRANPN-------PYTSRRSVASIVGTLVRMAPVIGA-CMARQ SEQID5   GQRADVYNMSFYDARPVIELILSK
         :: :::  |: :: |     ::|
pt.pep   AESSEA-MAAWSERAGEAMVLVYYESIAYSF (SEQ ID NO: 29)
```

As described above, therefore, there is only a low level of overall identity with a known toxin, but key catalytic residues are conserved.

In addition, a protein (SEQ ID 9) upstream gene in *S. typhimurium* shows homology to the pertussis toxin S2 subunit:

```
Score = 34.0 bits (77), Expect = 0.91
Identities = 31/101 (30%), Positives = 42/101 (40%), Gaps = 7/101 (6%)

Query:   30  TNAYYSDEVISELHVGQIDTSPYFCIKTVKANGSGTPVV-ACAVSKQSIWAPSFKELLDQ   88
             T+ YYS+   + L      T+    C    V+    SG PV+ AC        +   +  L
Sbjct:   98  TDHYYSNVTATRLLS---STNSRLCAVFVR---SGQPVIGACTSPYDGKYWSMYSTLRKM  151

Query:   89  ARYFYSTGQSVRIHVQKNIWTYPLFVNTFSANALVGLSSCS                    129  (SEQ ID NO: 9)
                 Y  G SVR+HV K     Y       TF    AL G+S C+
Sbjct:  152  LYLIYVAGISVRVHVSKEEQYYDYEDATFETYALTGISICN                    192  (SEQ ID NO: 30)
```

Toxin Gene from *Salmonella paratyphi* A (Strain ATCC 9150)

A protein with amino acid sequence <SEQ ID 6> was identified in *S. paratyphi*. This shows good homology to the *S. typhimurium* sequence shown above:

```
Score = 1231 (438.4 bits), Expect = 1.6e-125, P = 1.6e-125
Identities = 241/242 (99%) , Positives = 241/242 (99%)
Typhi:   1 MKKLIFLTLSIVSFNNYAVDFVYRVDSTPPDVIFRDGFSLLGYNRNFQQFISGRSCSGGS 60
           MKKLIFLTLSIVSPNNYAVDFVYRVDSTPPDVIFRDGFSLLGYNRNFQQFISGRSCSGGS
Parat:   1 MKKLIFLTLSIVSPNNYAVDFVYRVDSTPPDVIFRDGFSLLGYNRNFQQFISGRSCSGGS 60

Query:  61 SDSRYIATTSSVNQTYAIARAYYSRSTFKGNLYRYQIRADNNFYSLLPSITYLETQGGHF 120
           SDSRYIATTSSVNQTYAIARAYYSRSTFKCNLYRYQIRADNNFYSLLPSITYLETQGGHF
Sbjct:  61 SDSRYIATTSSVNQTYAIARAYYSRSTFKGNLYRYQIRADNNFYSLLPSITYLETQGGHF 120

Query: 121 NAYEKTMNRLQREYVSTLSILPENIQKAVALVYDSATGLVKDGVSTMNASYLGLSTTSNP 180
           NAYEKTMMRLQREYVSTLSILPENIQKAVALVYDSATGLVKDGVSTMNASYLGLSTTSNP
Sbjct: 121 NAYEKTMMRLQREYVSTLSILPENIQKAVALVYDSATGLVKDGVSTMNASYLGLSTTSNP 180

Query: 181 GVIPFLPEPQTYTQQRIXAFGPLISSCFSIGSVCHSHRGQRADVYNMSFYDARPVIELIL 240
           GVIPFLPEPQTYTQQRI AFGPLISSCPSIGSVC SHRGQRADVYNMSFYDARPVIELIL
Sbjct: 181 GVIPFLPEPQTYTQQRIDAFGPLISSCFSIGSVCQSHRGQRADVYNMSFYDARPVIELIL 240

Query: 241 SK* 242
           SK*
Sbjct: 241 SK* 242
```

Again, this protein shows only a low level of overall identity with a known toxin, but key catalytic residues are conserved.

As for *S. typhimurium*, there is an upstream PT-S2 homolog, but it is frame-shifted:

```
Score = 387 (141.3 bits), Expect = 4.9e-36, P = 4.9e-36
Identities = 73/73 (100%), Positives = 73/73 (100%), Frame = +3
Query:     65 TPVVACAVSKQSIWAPSFKELLDQARYFYSTGQSVRIHVQKNIWTYPLFVNTFSANALVG    124
              TPVVACAVSKQSIWAPSFKELLDQARYFYSTGQSVRIHVQKNIWTYPLFVNTFSANALVG
Sbjct:  14802 TPVVACAVSKQSIWAPSFKELLDQARYFYSTGQSVRIHVQKNIWTYPLFVNTFSANALVG  14981
Query:    125 LSSCSATQCFGPK                                                137 (SEQ ID NO: 9)
              LSSCSATQCFGPK
Sbjct:  14982 LSSCSATQCFGPK                                              15020 (SEQ ID NO: 31)
Score = 327 (120.2 bits), Expect = 1.1e-29, P = 1.1e-29
Identities = 65/96 (67%), Positives = 73/96 (76%), Frame = +1
Query:      1 MYMSKYVPVYTLLILIYSFNASAEWTGDNTNAYYSDEVISELHVGQIDTSPYFCIKTVKA     60
              MY++K+VPVYTLLILIYSFNASAEWTGDNTNAYYSDEVISELHVGQIDTSPYFCIKTVKA
Sbjct:  14611 MYINKFVPVYTLLILIYSFNASAEWTGDNTNAYYSDEVISELHVGQIDTSPYFCIKTVKA  14790
Query:     61 NGSGTPVVACAVSKQSIWAPSFKELLDQARYFYSTG                          96 (SEQ ID NO: 9)
              NGS  ++       ++    P  K L +    F  G
Sbjct:  14791 NGSVHQLLHVRYQSRAYGRPPLKNFLIRQDIFTVQG                       14898 (SEQ ID NO: 32)
```

Toxin Gene from *Streptococcus pyogenes*

A protein with the amino acid sequence <SEQ ID 7> was identified in *S. pyogenes*. This is encoded by a gene having nucleotide sequence <SEQ ID 8>.

This protein shows 24% identity to the C3 toxin from *Clostridium limosum*:

```
SEQID7         MLKKRYQLAIVLLLSCFSLIWQTEGLVELFVCEHYERAVCEGTP---AYFTFSDQKGA
               | :|    :  |  ||    ::||    :||:    |    ::  |   |:: |
exoc3_cloli.   MNKLTERVLCVGVSGLILFSVAALVQGTKKCYANPVRNRAASRVKPYADSFKEFTNIDEA SEQID7         ETLIKKRWGKGLITPRAEQEAMAAYTCQQAGPINTSLDKAKGELSQLTPELRDQVAQLDA
               ::   |:::|   :   :|::|:: ||  ::|: ||    | :|:  |   ::| :|:|
exoc3_cloli.   RAWGDKQFAKYKL-SSSEKNALTIYT-RNAARINGPLRANQGNTNGLPADIRKEVEQIDK SEQID7         ATHRLVIPWNIVVYRYVYETFLRDIGVSHADL--TSYYRNHQFDPHILCKIKL---GTRY
               :  ::  | ||:::|          ||    |:  |:    |:    |:   ::|    |
exoc3_cloli.   SFTKMQTPENIILFRG------DDPGYLGPDFENTILNRDGTINKAVFEQVKLRFKGKDR SEQID7         TKHSFMSTTALKNGAMTHRPVEVRICVKKGAKAAFVEPYSAVPSEVELLFPRGCQLEVVG
               :::::||:  ::::|:::   ||| :::  |   |:||::||  |:  :::|||   :
exoc3_cloli.   KEYGYISTSLVNGSAFAGRPIITKFKVLDGSKAGYIEPISTFKGQLEVLLPRSSTYTISD
```

```
                          -continued
SEQID7       AYVSQDQKKLHIEAYFKGSL  (SEQ ID NO: 7)
             :: ::|:: | | :|
exoc3_cloli. MQIAPNNKQIIITALLKR   (SEQ ID NO: 33)
```

It also shows 29% identity to the EDIN transferase [M63917; ref. 23] of *S. aureus*:

```
Indentities = 58/195 (29%), Positives = 106/195 (53%), Gaps = 13/195 (6%)

Query:  67 RWGKGLI----YPRAEQEAMAAYTCQQAGPINTSLDKAKGELSQLTPELRDQVAQLDAAT 122
           +WG LI    Y   ++ A+  YT + +   IN  L  A G+++L     +D+V +LD++
Sbjct:  49 KWGNKLIKQAKYSSDDKIALYEYT-KDSSKINGPLRLAGGDINKLDSTTQDKVRRLDSSI 107

Query: 123 HRLVIPWNIVVYRYVYETFLRDI-GVSHADLTSYYR--NHQFDPHILCKIK--LGTR-YT 176
           +   P ++ VYR +   +L  I G ++ DL    +   N Q+D +++ K+    + +R Y
Sbjct: 108 SKSTTPESVYVYRLLNLDYLTSIVGFTNEDLYKLQQTNNGQYDENLVRKLNNVMNSRIYR 167

Query: 177 KHSFMSTTALKNGAMTHRPVEVRICVKKGAKAAFV--EPYSAVPSEVELLFPRGCQLEVV 234
           +  + ST   +  A+  RP+E+R+ + KG KAA++  +  +A   + E+L PRG + V
Sbjct: 168 EDGYSSTQLVSGAAVGGRPIELRLELPKGTKAAYLNSKDLTAYYGQQEVLLPRGTEYAVG 227

Query: 235 GAYVSQDQKKLHIEA                                              249 (SEQ ID NO: 7)
           +S D+KK+ I A
Sbjct: 228 SVELSNDKKKIIITA                                              242 (SEQ ID NO: 34)
```

Enzymatic Studies

The *N. meningitidis* protein was expressed in and purified from *E. coli* as a His-tagged product. Mouse polyclonal antibodies raised against the recombinant protein were used in Western blot analysis and showed a sharp band at 20 kDa in a cell lysate of *N. meningitidis* strain MC58. A preparation of outer membrane vesicles showed no such band.

As a preliminary assay for NAD-glycohydrolase activity, agmatine was used as an ADP-ribose acceptor. Purified protein was incubated in the presence of 0 mM, 20 mM or 75 mM agmatine in 50 mM potassium phosphate, 0.01 mM [carbonyl-$^{14}$C]NAD (0.05 µCi), pH 7.5, in a total volume of 0.3 ml. After incubations at 30° C. for 18 hrs, samples (100 µl) were applied to 1 ml column of Dowex AG 1-X2. [$^{14}$C]Nicotinamide was eluted with 5 ml of H$_2$O for radioassay.

Enzymatic activity was as follows:

| Agmatine concentration (mM) | Enzymatic activity (pmoles/hr) |
|---|---|
| 0 | 34 |
| 20 | 62 |
| 75 | 72 |

Further studies of NAD-glycohydrolase and ADP-ribosyltransferase activity were performed using agmatine as acceptor. The NAD-glycohydrolase assay used 0.1M [carbonyl-$^{14}$C]NAD, which was replaced with [adenine-U-$^{14}$C]NAD for the ADP-ribosyltransferase assay. After incubation at 30° C. for 1 hour, samples were tested as before. Results were as follows:

| [Agmatine] (mM) | ADP-ribosylagmatine formed (nmol/hour) | Nicotinamide released (nmol/hour) |
|---|---|---|
| 0 | — | 8.9 |
| 20 | 6.3 | 15.4 |
| 75 | 18.1 | 25.9 |

Further amino acids were tested as ADP-ribose acceptors at 20 mM concentration. Results were:

| Amino acid | Nicotinamide released (nmol/hour) |
|---|---|
| Control | 8.2 |
| Agmatine | 15.6 |
| Arginine | 14.6 |
| Glycine | 8.5 |
| Cysteine | 11.7 |
| Serine | 8.6 |
| Lysine | 8.9 |
| Histidine | 8.8 |
| Proline | 8.6 |

Auto ADP-Ribosylation of *N. meningitidis* Toxin

Purified NMB1343 (5.7 µg) was incubated in 50 mM potassium phosphate (pH 7.5) with 10 µM [adenylate-$^{32}$P]NAD (10 µCi per assay) in a total volume of 50 µl for 1 h at 30° C. Protein was precipitated with the addition of 50 µl of ice-cold trichloroacetic acid (final concentration 25%) and, following an overnight incubation at 4° C., was collected by centrifugation (10,000×g for 30 min). The pellet was suspended in LDS and heated at 70° C. for 5 min. Samples were then subjected to electrophoresis in (4-12% or 10%) NuPAGE gels using MES as running buffer and electrotransferred to nitrocellulose membranes that were exposed to X-Omat film for 5 days at room temperature.

Figure 3A:
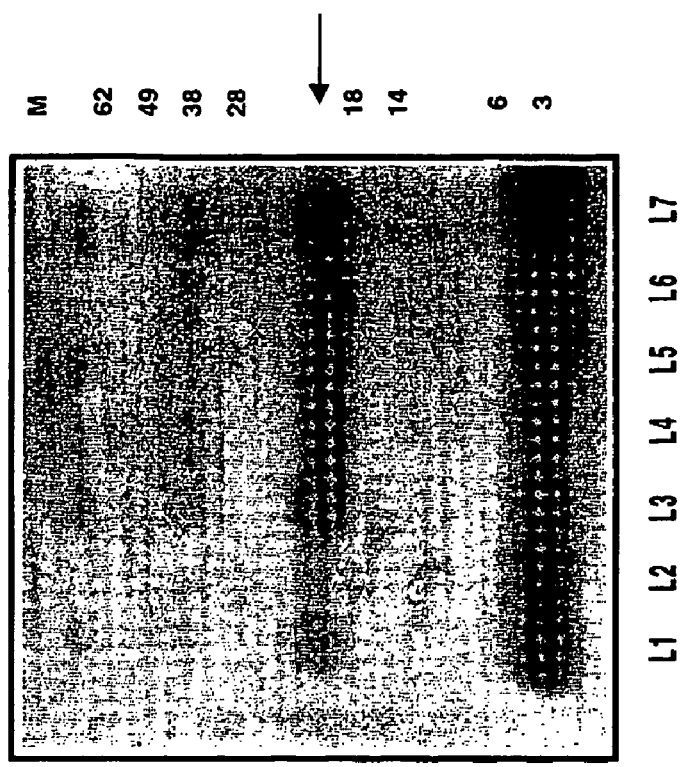
FIG. 3 shows the incorporation of radio-labelled NAD into the *N. meningitidis* toxin.

During incubation with [$^{32}$P]NAD, the radiolabel of NMB1343 increases in a concentration dependent manner (FIG. 3A). To confirm that protein modification was enzymatic (i.e. that chemical addition of reactive ADP-ribose was not involved), labelling experiments were carried out in the presence of Nam, a known NADase inhibitor and in the presence of a large excess of cold ADP-ribose. Both experiments gave an identical amount of radiolabelled protein (FIG. 3B, L5 & L6). Enzymatic incorporation was also supported by the finding that pre-incubation of NMB1343 at 95° C. for 5 minutes completely abolishes labelling (L1) and that labelling does not occur in the presence of novobiocin (L2), a known inhibitor of ADPRTs.

Mutant Toxins

Based on homology with known toxins and the prediction of catalytic residues, four mutants SEQ ID 1 were generated, each containing a single amino acid substitution. The arginine in position 7 and the glutamic acids in positions 109, 111 and 120 were replaced with lysine and glycine residues respectively, using PCR-based site-directed mutagenesis (SDM). Internal primers containing a codon change from Arg to Lys, and from Glu to Gly were designed:

| Primer | Sequence | {SEQ ID} | Codon change |
|---|---|---|---|
| WT-for | CGCGGATCCCATATGGGAAATTTCTT ATATAGAGGCATTAGTTGC | {18} | |
| WT-rev | CCCGCTCGAGGTTAATTTCTATCAAC TCTTTAGCAAT | {19} | |
| R7K-for | CGCGGATCCCATATGGGAAATTTCTT ATATAaAGGCATTAGTTGC | {20} | AGA → AaA |
| E109G-for | ATTTTTGAATATGgGTTGAACATCCA GAAAAC | {21} | GAG → GgG |
| E109G-rev | TTCTGGATGTTCAACCcCATATTCAA AAATAGA | {22} | |
| E111G-for | TATGAGGTTGgACATCCAGAA AACCCA | {23} | GAA → GgA |
| E111G-rev | GTTTTCTGGATGTcCAACCTC ATATTC | {24} | |
| E120G-for | CCAAATGAGAAGGgAGTAACA ATCAGAG | {25} | GAA → GgA |
| E120G-rev | GATTGTTACTcCCTTCTCATT TGGGTT | {26} | |

Underlined nucleotides code for lysine or glycine, and mutated nucleotides are in lower case.

To generate the R7K mutant, a single step of PCR was performed. The template was 20 ng of DNA which encodes his-tagged NMB1343. Primers were R7K- for and WT-rev.

To generate the remaining mutants, PCR was performed using 20 ng of pET 21b+ DNA as template, and the following primer pairs: (1) WT- for/E109G-rev; (2) E109G- for/WT-rev; (3) WT- for E111G-rev; (4) E111G- for/WT-rev; (5) WT- for/E120G-rev; (6) E120G- for/WT-rev.

The second round of PCR was performed using the product of PCR 1-2, 3-4 or 5-6 as template, and WT- for and WT-rev as forward and reverse primers, respectively.

The PCR fragments containing each mutation were processed following standard procedure, digested with, NdeI and XhoI restriction enzymes and cloned into pET-21b+ vector. The presence of each mutation was confirmed by sequence analysis.

After cloning each gene into the expression vector, recombinant plasmids were transformed into *E. coli* strains suitable for expression of the recombinant protein as His-tag. 1.5 µl of each construct was used to transform *E. coli* BL21-DE3. Single recombinant colonies were inoculated into 4 ml LB+Amp (100 µg/ml), incubated at 37° C. overnight, then diluted 1:30 in 20 ml of LB+Amp (100 µg/ml) in 125 ml flasks, to give an $OD_{600}$ between 0.1 and 0.2. The flasks were incubated at 37° C. in a gyratory water bath shaker until $OD_{600}$ indicated exponential growth suitable for induction of expression (0.4-0.8 OD). Protein expression was induced by addition of 1.0 mM IPTG. After 3 hours incubation at 37° C. the $OD_{600}$ was measured and expression examined. 1.0 ml of each sample was centrifuged in a microfuge, the pellet resuspended in PBS and analysed by SDS-PAGE and Coomassie Blue staining. All the mutants were expressed as efficiently as wild-type, and they were purified as soluble forms.

ADP-ribosyltransferase and NAD-glycohydrolase activities were determined as described above. The Lys and Gly mutations were studied separately. Results were as follows:

| Mutant | ADP-ribosyltransferase activity (pmol/hour) | AND-glycohydrolase activity (nmol/hour) |
|---|---|---|
| Wild type | 1.8 | 2.6 |
| R7K | 0.1 | 0.08 |
| Wild type | 305 | 680 |
| E109G | 30 | 315 |
| E111G | 116 | 289 |
| E120G | 36 | 100 |

Thus the enzymatic activity of the *N. meningitidis* toxin can be rationally and efficiently removed by site-directed mutagenesis.

It will be understood that the invention has been described by way of example only and modifications may be made whilst remaining within the scope and spirit of the invention.

TABLE 1 preferred mutations (Δ = deletion of the residue)

| SEQ ID | Site for mutation(s) | Replacement residue |
|---|---|---|
| 1 | Arg-7 | Lys, Δ |
| | Lys-24 | Gly, Trp |
| | Tyr-34 | Trp, Ala, His |
| | His-57 | Asn, Tyr, Gln, Val, Ser, Pro |
| | Glu-60 | Ala |
| | Thr-61 | Gly |
| | Tyr-68 | Met, Glu |
| | Ser-70 | Phe |
| | Thr-72 | Lys, Tyr |
| | Ala-82 | Arg |
| | Gly-86 | Lys |
| | Tyr-103 | Lys, Asp, Ser |
| | Glu-107 | Asp, Ser, Δ |
| | Glu-109 | Ala, Gly, Lys, Asp, Ser, Δ |
| | Glu-111 | Ala, Gly, Lys, Asp, Gln, Δ |
| | Glu-118 | Asp, Ser, Δ |
| | Glu-120 | Ala, Gly, Lys, Asp, Gln, Δ |
| 3 | Asp-64 | Glu, Tyr |
| | Arg-81 | Lys, Gly, Trp, Δ |
| | Asp-83 | Glu, Tyr, Ser |
| | Arg-85 | Lys, His, Leu |
| | Gly-86 | Arg, Asp |
| | His-96 | Asn, Tyr, Gln, Val, Ser, Pro |
| | Gln-101 | Ala |
| | Tyr-110 | Met |
| | Val-113 | Asp, Glu, Tyr |
| | Tyr-119 | Glu |
| | Ser-121 | Phe |
| | Ser-123 | Lys, Tyr |
| | His-126 | Asn, Tyr, Gln, Val |
| | Gly-136 | Lys |
| | Val-149 | Lys, Tyr |
| | His-157 | Glu |
| | Gln-162 | Asp, Ser, Δ |
| | Glu-164 | Ala, Gly, Lys, Asp, Gln, Δ |
| 4 | Arg-10 | Lys, Δ |
| | Asp-12 | Glu, Tyr, Ser |
| | Arg-14 | Lys, His, Leu |
| | Ile-19 | Ala |
| | His-36 | Asn, Tyr, Gln, Val, Ser, Pro |
| | Thr-40 | Gly |
| | Arg-44 | Ala, Lys |
| | Phe-47 | Met, Glu |
| | Ser-49 | Phe |
| | Ser-51 | Lys, Tyr |
| | Ala-57 | Arg |
| | Gln-130 | Asp, Ser, Δ |
| | Glu-132 | Ala, Gly, Lys, Asp, Gln, Δ |
| | Trp-133 | Gly |

TABLE 1-continued preferred mutations (Δ = deletion of the residue)

| SEQ ID | Site for mutation(s) | Replacement residue |
|---|---|---|
| 5/6 | Arg-24 | Lys, Δ |
| | Asp-26 | Glu, Tyr, Ser |
| | Ile-33 | Ala |
| | Tyr-43 | Trp, Ala, His |
| | Arg-46 | Ala, Lys |
| | Cys-56 | Δ |
| | Ser-61 | Phe |
| | Ser-63 | Lys, Tyr |
| | Tyr-65 | Met, Glu |
| | Thr-68 | Phe |
| | Thr-69 | Phe |
| | Ser-70 | Lys, Tyr |
| | Ser-84 | Phe |
| | Ser-86 | Lys, Tyr |
| | Gln-131 | Asp, Ser, Δ |
| | Glu-133 | Gly, Ala, Lys, Asp, Gln, Δ |
| | Tyr-134 | Gly |
| 7 | Arg-130 | Lys, Δ |
| | Ser-177 | Phe |
| | Thr-179 | Lys, Tyr |
| | Cys-196 | Ser |
| | Glu-215 | Ser, Asp, Δ |
| | Glu-217 | Gly, Ala, Lys, Asp, Gln, Δ |

REFERENCES

The Contents of which are Hereby Incorporated in Full

[1] Rappuoli & Pizza (1991) Chapter 1 of *Sourcebook of Bacterial Protein Toxins* (Alouf & Freer, eds). ISBN 0-12-053078-3.
[2] Bazan & Koch-Nolte (1997) *Adv. Exp. Med. Biol.* 419:99-107.
[3] Sixma et al. (1991) *Nature* 351:371-377.
[4] Zhang et al. (1995) *J. Mol. Biol.* 251:563-573.
[5] Stein et al. (1994) *Structure* 2:45-57.
[6] International patent application WO93/13202.
[7] European patent applications 0306618, 0322533 and 0322115.
[8] Del Guidice & Rappuoli (1999) *Vaccine* 1999 17 Suppl 2:S44-52
[9] European patent 0396964.
[10] Northrup & Fauci (1972) *J. Infect. Dis.* 125:672ff.
[11] Elson & Ealding (1984) *J. Immunol.* 133:2892ff and 132:2736ff
[12] International patent application WO95/17211.
[13] van den Akker et al. (1997) *Protein Sci* 6:2644-2649.
[14] International patent application WO99/24578.
[15] International patent application WO99/36544.
[16] International patent application WO99/57280.
[17] Tettelin et al. (2000) *Science* 287:1809-1815.
[18] Pizza et al. (2000) *Science* 287:1816-1820.
[19] International patent application WO01/64920.
[20] International patent application WO01/64922.
[21] Parkhill et al. (2000) *Nature* 404:502-506.
[22] Himmelreich et al. (1996) *Nucleic Acids Res.* 24:4420-4449.
[23] Wilde et al. (2001) *J. Biol. Chem.* 276:9537-9542.

The invention claimed is:

1. An isolated adenosine diphosphate-ribosylating (ADP-ribosylating) polypeptide comprising an amino acid sequence having at least 95% sequence identity to the amino acid sequence set forth in SEQ ID NO:1, wherein the polypeptide comprises at least one mutation compared to the amino acid sequence set forth in SEQ ID NO:1, and wherein the at least one mutation reduces or eliminates the ADP-ribosylating activity of the polypeptide compared to that of a wild-type polypeptide.

2. The polypeptide of claim 1, wherein said at least one mutation is selected from the group consisting of Arg7Lys, Δ; Lys24Gly, Trp; Tyr34Trp, Ala, His; His57Asn, Tyr, Gln, Val, Ser, Pro; Glu60Ala; Thr61Gly; Tyr68Met, Glu; Ser70Phe; Thr72Lys, Tyr; Ala82Arg; Gly86Lys; Tyr103Lys, Asp, Ser; Glu107Asp, Ser, Δ; Glu109Ala, Gly, Lys, Asp, Ser, Δ; Glu111Ala, Gly, Lys, Asp, Gln, Δ; Glu118Asp, Ser, Δ; and Glu120Ala, Gly, Lys, Asp, Gln, A, wherein Δ indicated deletion of the residue.

3. A composition comprising the polypeptide of claim 1 and a pharmaceutically acceptable carrier.

4. An isolated adenosine diphosphate-ribosvlatinq (ADP-ribosylating) polypeptide comprising an amino acid sequence having at least 99% sequence identity to the amino acid sequence set forth in SEQ ID NO:1, wherein the polypeptide comprises at least one mutation compared to the amino acid sequence set forth in SEQ ID NO:1, and wherein the at least one mutation reduces or eliminates the ADP-ribosylating activity of the polypeptide compared to that of a wild-type polypeptide.

5. The polypeptide of claim 4, wherein said at least one mutation is selected from the group consisting of Arg7Lys, Δ; Lys24Gly, Trp; Tyr34Trp, Ala, His; His57Asn, Tyr, Gln, Val, Ser, Pro; Glu60Ala; Thr61Gly; Tyr68Met, Glu; Ser70Phe; Thr72Lys, Tyr; Ala82Arg; Gly86Lys; Tyr103Lys, Asp, Ser; Glu107Asp, Ser, Δ; Glu109Ala, Gly, Lys, Asp, Ser, Δ; Glu111Ala, Gly, Lys, Asp, Gln, Δ; Glu118Asp, Ser, Δ; and Glu120Ala, Gly, Lys, Asp, Gin, Δ, wherein Δ indicated deletion of the residue.

* * * * *

SEQUENCE LISTING

<160> NUMBER OF SEQ ID NOS: 99

<210> SEQ ID NO 1
<211> LENGTH: 145
<212> TYPE: PRT
<213> ORGANISM: Neisseria meningitidis

<400> SEQUENCE: 1

Met Gly Asn Phe Leu Tyr Arg Gly Ile Ser Cys Gln Gln Asp Glu Gln
1               5                   10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Glu Val Glu His
            100                 105                 110

Pro Glu Asn Pro Asn Glu Lys Glu Val Thr Ile Arg Ala Glu Asp Cys
        115                 120                 125

Gly Cys Ile Pro Glu Glu Val Ile Ile Ala Lys Glu Leu Ile Glu Ile

```
                          130                 135                 140

Asn
145

<210> SEQ ID NO 2
<211> LENGTH: 435
<212> TYPE: DNA
<213> ORGANISM: Neisseria meningitidis

<400> SEQUENCE: 2
atgggaaatt tcttatatag aggcattagt tgccaacaag atgagcaaaa taatggacag      60
ttaaaaccta aaggtaataa agctgaagtt gcaattcgtt atgatggtaa gtttaaatat     120
gatggtaaag ctacacatgg tccaagtgtg aagaatgcag tttacgccca tcaaattgaa     180
acaggtctat atgacggatg ttatatatct acgacaacag acaaggaaat tgccaagaaa     240
tttgcaacaa gttccggcat cgaaaatggc tatatatatg ttttaaatag ggatttgttt     300
ggtcaatatt ctattttga atatgaggtt gaacatccaa aaacccaaa tgagaaggaa       360 gtaacaatca gagctgaaga ttgtggctgt attcctgaag aagtgattat tgctaaagag     420
ttgatagaaa ttaac                                                     435

<210> SEQ ID NO 3
<211> LENGTH: 204
<212> TYPE: PRT
<213> ORGANISM: Streptomyces coelicolor

<400> SEQUENCE: 3

Met Ile Thr Thr Ser Leu Arg Arg Arg Thr Ala Ala Ala Val Leu Ser
 1               5                  10                  15

Leu Ser Ala Val Leu Ala Thr Thr Ala Ala Thr Ala Pro Gly Ala Ala
             20                  25                  30

Pro Ala Pro Ser Ala Ala Pro Ala Lys Ala Ala Pro Ala Cys Pro Gln
         35                  40                  45

Phe Asp Asp Arg Thr Lys Ala Ala Ala Asp Arg Gly Val Asp Val Asp
     50                  55                  60

Arg Ile Thr Pro Glu Pro Val Trp Arg Thr Thr Cys Gly Thr Leu Tyr
 65                  70                  75                  80

Arg Ser Asp Ser Arg Gly Pro Gln Val Val Phe Glu Glu Gly Phe His
                 85                  90                  95

Ala Lys Asp Val Gln Asn Gly Gln Tyr Asp Val Glu Lys Tyr Val Leu
            100                 105                 110

Val Asn Gln Pro Ser Pro Tyr Val Ser Thr Ser Tyr Asp His Asp Leu
        115                 120                 125

Tyr Lys Thr Trp Tyr Lys Ser Gly Tyr Asn Tyr Tyr Val Asp Ala Pro
    130                 135                 140

Gly Gly Ile Asp Val Asn Lys Thr Ile Gly Asp Thr His Lys Trp Ala
145                 150                 155                 160

Asp Gln Val Glu Val Ala Phe Pro Gly Gly Ile Gln Arg Lys Tyr Ile
                165                 170                 175

Ile Gly Val Cys Pro Val Asp Arg Gln Thr Lys Thr Glu Ile Met Ser
            180                 185                 190

Asp Cys Glu Ser Asn Pro His Tyr Gln Pro Trp His
        195                 200

<210> SEQ ID NO 4
<211> LENGTH: 591
<212> TYPE: PRT
```

<213> ORGANISM: Mycoplasma pneumoniae

<400> SEQUENCE: 4

```
Met Pro Asn Pro Val Arg Phe Val Tyr Arg Val Asp Leu Arg Ser Pro
  1               5                  10                  15
Glu Glu Ile Phe Glu His Gly Phe Ser Thr Leu Gly Asp Val Arg Asn
             20                  25                  30
Phe Phe Glu His Ile Leu Ser Thr Asn Phe Gly Arg Ser Tyr Phe Ile
         35                  40                  45
Ser Thr Ser Glu Thr Pro Thr Ala Ala Ile Arg Phe Phe Gly Ser Trp
 50                  55                  60
Leu Arg Glu Tyr Val Pro Glu His Pro Arg Arg Ala Tyr Leu Tyr Glu
 65                  70                  75                  80
Ile Arg Ala Asp Gln His Phe Tyr Asn Ala Arg Ala Thr Gly Glu Asn
             85                  90                  95
Leu Leu Asp Leu Met Arg Gln Arg Gln Val Val Phe Asp Ser Gly Asp
            100                 105                 110
Arg Glu Met Ala Gln Met Gly Ile Arg Ala Leu Arg Thr Ser Phe Ala
        115                 120                 125
Tyr Gln Arg Glu Trp Phe Thr Asp Gly Pro Ile Ala Ala Ala Asn Val
130                 135                 140
Arg Ser Ala Trp Leu Val Asp Ala Val Pro Val Glu Pro Gly His Ala
145                 150                 155                 160
His His Pro Ala Gly Arg Val Val Glu Thr Thr Arg Ile Asn Glu Pro
            165                 170                 175
Glu Met His Asn Pro His Tyr Gln Glu Leu Gln Thr Gln Ala Asn Asp
        180                 185                 190
Gln Pro Trp Leu Pro Thr Pro Gly Ile Ala Thr Pro Val His Leu Ser
        195                 200                 205
Ile Pro Gln Ala Ala Ser Val Ala Asp Val Ser Glu Gly Thr Ser Ala
210                 215                 220
Ser Leu Ser Phe Ala Cys Pro Asp Trp Ser Pro Ser Ser Asn Gly
225                 230                 235                 240
Glu Asn Pro Leu Asp Lys Cys Ile Ala Glu Lys Ile Asp Asn Tyr Asn
            245                 250                 255
Leu Gln Ser Leu Pro Gln Tyr Ala Ser Ser Val Lys Glu Leu Glu Asp
        260                 265                 270
Thr Pro Val Tyr Leu Arg Gly Ile Lys Thr Gln Lys Thr Phe Met Leu
        275                 280                 285
Gln Ala Asp Pro Gln Asn Asn Asn Val Phe Leu Val Glu Val Asn Pro
290                 295                 300
Lys Gln Lys Ser Ser Phe Pro Gln Thr Ile Phe Phe Trp Asp Val Tyr
305                 310                 315                 320
Gln Arg Ile Cys Leu Lys Asp Leu Thr Gly Ala Gln Ile Ser Leu Ser
            325                 330                 335
Leu Thr Ala Phe Thr Thr Gln Tyr Ala Gly Gln Leu Lys Val His Leu
        340                 345                 350
Ser Val Ser Ala Val Asn Ala Val Asn Gln Lys Trp Lys Met Thr Pro
        355                 360                 365
Gln Asp Ile Ala Ile Thr Gln Phe Arg Val Ser Ser Glu Leu Leu Gly
    370                 375                 380
Gln Thr Glu Asn Gly Leu Phe Trp Asn Thr Lys Ser Gly Gly Ser Gln
385                 390                 395                 400
His Asp Leu Tyr Val Cys Pro Leu Lys Asn Pro Pro Ser Asp Leu Glu
```

```
                        405                 410                 415
Glu Leu Gln Ile Ile Val Asp Glu Cys Thr Thr His Ala Gln Phe Val
            420                 425                 430

Thr Met Arg Ala Ala Ser Thr Phe Phe Val Asp Val Gln Leu Gly Trp
        435                 440                 445

Tyr Trp Arg Gly Tyr Tyr Thr Pro Gln Leu Ser Gly Trp Ser Tyr
    450                 455                 460

Gln Met Lys Thr Pro Asp Gly Gln Ile Phe Tyr Asp Leu Lys Thr Ser
465                 470                 475                 480

Lys Ile Phe Phe Val Gln Asp Asn Gln Asn Val Phe Phe Leu His Asn
                485                 490                 495

Lys Leu Asn Lys Gln Thr Gly Tyr Ser Trp Asp Trp Val Glu Trp Leu
            500                 505                 510

Lys His Asp Met Asn Glu Asp Lys Asp Glu Asn Phe Lys Trp Tyr Phe
        515                 520                 525

Ser Arg Asp Asp Leu Thr Ile Pro Ser Val Glu Gly Leu Asn Phe Arg
    530                 535                 540

His Ile Arg Cys Tyr Ala Asp Asn Gln Gln Leu Lys Val Ile Ile Ser
545                 550                 555                 560

Gly Ser Arg Trp Gly Gly Trp Tyr Ser Thr Tyr Asp Lys Val Glu Ser
                565                 570                 575

Asn Val Glu Asp Lys Ile Leu Val Lys Asp Gly Phe Asp Arg Phe
            580                 585                 590

<210> SEQ ID NO 5
<211> LENGTH: 242
<212> TYPE: PRT
<213> ORGANISM: Salmonella typhimurium
<220> FEATURE:
<221> NAME/KEY: VARIANT
<222> LOCATION: 198
<223> OTHER INFORMATION: Xaa is any amino acid

<400> SEQUENCE: 5

Met Lys Lys Leu Ile Phe Leu Thr Leu Ser Ile Val Ser Phe Asn Asn
1               5                   10                  15

Tyr Ala Val Asp Phe Val Tyr Arg Val Asp Ser Thr Pro Pro Asp Val
            20                  25                  30

Ile Phe Arg Asp Gly Phe Ser Leu Leu Gly Tyr Asn Arg Asn Phe Gln
        35                  40                  45

Gln Phe Ile Ser Gly Arg Ser Cys Ser Gly Ser Ser Asp Ser Arg
    50                  55                  60

Tyr Ile Ala Thr Thr Ser Ser Val Asn Gln Thr Tyr Ala Ile Ala Arg
65                  70                  75                  80

Ala Tyr Tyr Ser Arg Ser Thr Phe Lys Gly Asn Leu Tyr Arg Tyr Gln
                85                  90                  95

Ile Arg Ala Asp Asn Asn Phe Tyr Ser Leu Leu Pro Ser Ile Thr Tyr
            100                 105                 110

Leu Glu Thr Gln Gly Gly His Phe Asn Ala Tyr Glu Lys Thr Met Met
        115                 120                 125

Arg Leu Gln Arg Glu Tyr Val Ser Thr Leu Ser Ile Leu Pro Glu Asn
    130                 135                 140

Ile Gln Lys Ala Val Ala Leu Val Tyr Asp Ser Ala Thr Gly Leu Val
145                 150                 155                 160

Lys Asp Gly Val Ser Thr Met Asn Ala Ser Tyr Leu Gly Leu Ser Thr
                165                 170                 175
```

```
Thr Ser Asn Pro Gly Val Ile Pro Phe Leu Pro Glu Pro Gln Thr Tyr
            180                 185                 190

Thr Gln Gln Arg Ile Xaa Ala Phe Gly Pro Leu Ile Ser Ser Cys Phe
        195                 200                 205

Ser Ile Gly Ser Val Cys His Ser His Arg Gly Gln Arg Ala Asp Val
    210                 215                 220

Tyr Asn Met Ser Phe Tyr Asp Ala Arg Pro Val Ile Glu Leu Ile Leu
225                 230                 235                 240

Ser Lys

<210> SEQ ID NO 6
<211> LENGTH: 242
<212> TYPE: PRT
<213> ORGANISM: Salmonella paratyphi

<400> SEQUENCE: 6

Met Lys Lys Leu Ile Phe Leu Thr Leu Ser Ile Val Ser Phe Asn Asn
1               5                   10                  15

Tyr Ala Val Asp Phe Val Tyr Arg Val Asp Ser Thr Pro Pro Asp Val
            20                  25                  30

Ile Phe Arg Asp Gly Phe Ser Leu Leu Gly Tyr Asn Arg Asn Phe Gln
        35                  40                  45

Gln Phe Ile Ser Gly Arg Ser Cys Ser Gly Ser Ser Asp Ser Arg
    50                  55                  60

Tyr Ile Ala Thr Thr Ser Ser Val Asn Gln Thr Tyr Ala Ile Ala Arg
65                  70                  75                  80

Ala Tyr Tyr Ser Arg Ser Thr Phe Lys Gly Asn Leu Tyr Arg Tyr Gln
                85                  90                  95

Ile Arg Ala Asp Asn Asn Phe Tyr Ser Leu Leu Pro Ser Ile Thr Tyr
            100                 105                 110

Leu Glu Thr Gln Gly Gly His Phe Asn Ala Tyr Glu Lys Thr Met Met
        115                 120                 125

Arg Leu Gln Arg Glu Tyr Val Ser Thr Leu Ser Ile Leu Pro Glu Asn
    130                 135                 140

Ile Gln Lys Ala Val Ala Leu Val Tyr Asp Ser Ala Thr Gly Leu Val
145                 150                 155                 160

Lys Asp Gly Val Ser Thr Met Asn Ala Ser Tyr Leu Gly Leu Ser Thr
                165                 170                 175

Thr Ser Asn Pro Gly Val Ile Pro Phe Leu Pro Glu Pro Gln Thr Tyr
            180                 185                 190

Thr Gln Gln Arg Ile Asp Ala Phe Gly Pro Leu Ile Ser Ser Cys Phe
        195                 200                 205

Ser Ile Gly Ser Val Cys Gln Ser His Arg Gly Gln Arg Ala Asp Val
    210                 215                 220

Tyr Asn Met Ser Phe Tyr Asp Ala Arg Pro Val Ile Glu Leu Ile Leu
225                 230                 235                 240

Ser Lys

<210> SEQ ID NO 7
<211> LENGTH: 250
<212> TYPE: PRT
<213> ORGANISM: Streptococcus pyogenes

<400> SEQUENCE: 7

Met Leu Lys Lys Arg Tyr Gln Leu Ala Ile Val Leu Leu Leu Ser Cys
1               5                   10                  15
```

```
Phe Ser Leu Ile Trp Gln Thr Glu Gly Leu Val Glu Leu Phe Val Cys
             20                  25                  30

Glu His Tyr Glu Arg Ala Val Cys Glu Gly Thr Pro Ala Tyr Phe Thr
         35                  40                  45

Phe Ser Asp Gln Lys Gly Ala Glu Thr Leu Ile Lys Lys Arg Trp Gly
 50                  55                  60

Lys Gly Leu Ile Tyr Pro Arg Ala Glu Gln Glu Ala Met Ala Ala Tyr
 65                  70                  75                  80

Thr Cys Gln Gln Ala Gly Pro Ile Asn Thr Ser Leu Asp Lys Ala Lys
                 85                  90                  95

Gly Glu Leu Ser Gln Leu Thr Pro Glu Leu Arg Asp Gln Val Ala Gln
            100                 105                 110

Leu Asp Ala Ala Thr His Arg Leu Val Ile Pro Trp Asn Ile Val Val
        115                 120                 125

Tyr Arg Tyr Val Tyr Glu Thr Phe Leu Arg Asp Ile Gly Val Ser His
130                 135                 140

Ala Asp Leu Thr Ser Tyr Tyr Arg Asn His Gln Phe Asp Pro His Ile
145                 150                 155                 160

Leu Cys Lys Ile Lys Leu Gly Thr Arg Tyr Thr Lys His Ser Phe Met
                165                 170                 175

Ser Thr Thr Ala Leu Lys Asn Gly Ala Met Thr His Arg Pro Val Glu
            180                 185                 190

Val Arg Ile Cys Val Lys Lys Gly Lys Ala Ala Phe Val Glu Pro
        195                 200                 205

Tyr Ser Ala Val Pro Ser Glu Val Glu Leu Leu Phe Pro Arg Gly Cys
    210                 215                 220

Gln Leu Glu Val Val Gly Ala Tyr Val Ser Gln Asp Gln Lys Lys Leu
225                 230                 235                 240

His Ile Glu Ala Tyr Phe Lys Gly Ser Leu
                245                 250

<210> SEQ ID NO 8
<211> LENGTH: 765
<212> TYPE: DNA
<213> ORGANISM: Streptococcus pyogenes

<400> SEQUENCE: 8
gtgtcagggg gaactatgct aaaaaagcgc tatcaactgg ctattgtcct tcttcttagc      60
tgttttagtc tgatctggca aactgagggc ttggtcgagc ttttttgtctg tgagcactat    120 gagcgggcgg tttgtgaggg gacgcctgct tattttacct tttcggatca aaagggcgct    180
gagacactga ttaaaaagcg atggggcaag ggtctcatct acccaagggc tgagcaagag    240
gcgatggctg cttatacctg tcagcaggca ggccctatca acaccagcct agacaaagcc    300
aaaggtgagc tcagccaact cacgcctgag ctaagggatc aggtggccca gctcgatgct    360
gcgactcacc ggctagtcat cccgtggaac attgtagtat accgctatgt atacgagacg    420 ttttgcgtg atatcggtgt ttcacatgct gatctcacgt cttactaccg taaccatcag    480
tttgaccctc atatcctttg taagatcaag cttggtacac gctacaccaa gcacagtttt    540
atgagcacga cagccttgaa aaacggcgcc atgacccatc gaccggtgga ggtgcgcatc    600
tgtgtcaaaa aggggccaa ggcagccttt gtcgagcctt attcggctgt gccttcagag    660
gttgagctct gtttccaag aggctgtcag ctggaggtcg ttggagctta cgtgtcacag    720
gaccaaaaaa agctccacat agaagcgtat ttcaagggca gtttg                    765
```

```
<210> SEQ ID NO 9
<211> LENGTH: 137
<212> TYPE: PRT
<213> ORGANISM: Salmonella typhimurium

<400> SEQUENCE: 9

Met Tyr Met Ser Lys Tyr Val Pro Val Tyr Thr Leu Leu Ile Leu Ile
1               5                   10                  15

Tyr Ser Phe Asn Ala Ser Ala Glu Trp Thr Gly Asp Asn Thr Asn Ala
            20                  25                  30

Tyr Tyr Ser Asp Glu Val Ile Ser Glu Leu His Val Gly Gln Ile Asp
        35                  40                  45

Thr Ser Pro Tyr Phe Cys Ile Lys Thr Val Lys Ala Asn Gly Ser Gly
    50                  55                  60

Thr Pro Val Val Ala Cys Ala Val Ser Lys Gln Ser Ile Trp Ala Pro
65                  70                  75                  80

Ser Phe Lys Glu Leu Leu Asp Gln Ala Arg Tyr Phe Tyr Ser Thr Gly
                85                  90                  95

Gln Ser Val Arg Ile His Val Gln Lys Asn Ile Trp Thr Tyr Pro Leu
            100                 105                 110

Phe Val Asn Thr Phe Ser Ala Asn Ala Leu Val Gly Leu Ser Ser Cys
        115                 120                 125

Ser Ala Thr Gln Cys Phe Gly Pro Lys
    130                 135

<210> SEQ ID NO 10
<211> LENGTH: 145
<212> TYPE: PRT
<213> ORGANISM: Neisseria meningitidis

<400> SEQUENCE: 10

Met Gly Asn Phe Leu Tyr Lys Gly Ile Ser Cys Gln Gln Asp Glu Gln
1               5                   10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Glu Val Glu His
            100                 105                 110

Pro Glu Asn Pro Asn Glu Lys Glu Val Thr Ile Arg Ala Glu Asp Cys
        115                 120                 125

Gly Cys Ile Pro Glu Glu Val Ile Ile Ala Lys Glu Leu Ile Glu Ile
    130                 135                 140

Asn
145

<210> SEQ ID NO 11
<211> LENGTH: 435
<212> TYPE: DNA
<213> ORGANISM: Neisseria meningitidis

<400> SEQUENCE: 11
```

```
atgggaaatt tcttatataa aggcattagt tgccaacaag atgagcaaaa taatggacag    60
ttaaaaccta aagtaataa agctgaagtt gcaattcgtt atgatggtaa gtttaaatat   120
gatggtaaag ctacacatgg tccaagtgtg aagaatgcag tttacgccca tcaaattgaa   180
acaggtctat atgacggatg ttatatatct acgacaacag acaaggaaat tgccaagaaa   240
tttgcaacaa gttccggcat cgaaaatggc tatatatatg ttttaaatag ggatttgttt   300
ggtcaatatt ctattttga atatgaggtt gaacatccag aaaacccaaa tgagaaggaa   360
gtaacaatca gagctgaaga ttgtggctgt attcctgaag aagtgattat tgctaaagag   420
ttgatagaaa ttaac                                                   435
```

<210> SEQ ID NO 12
<211> LENGTH: 145
<212> TYPE: PRT
<213> ORGANISM: Neisseria meningitidis

<400> SEQUENCE: 12

```
Met Gly Asn Phe Leu Tyr Arg Gly Ile Ser Cys Gln Gln Asp Glu Gln
 1               5                  10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Gly Val Glu His
            100                 105                 110

Pro Glu Asn Pro Asn Glu Lys Glu Val Thr Ile Arg Ala Glu Asp Cys
        115                 120                 125

Gly Cys Ile Pro Glu Glu Val Ile Ile Ala Lys Glu Leu Ile Glu Ile
    130                 135                 140

Asn
145
```

<210> SEQ ID NO 13
<211> LENGTH: 435
<212> TYPE: DNA
<213> ORGANISM: Neisseria meningitidis

<400> SEQUENCE: 13

```
atgggaaatt tcttatatag aggcattagt tgccaacaag atgagcaaaa taatggacag    60
ttaaaaccta aagtaataa agctgaagtt gcaattcgtt atgatggtaa gtttaaatat   120
gatggtaaag ctacacatgg tccaagtgtg aagaatgcag tttacgccca tcaaattgaa   180
acaggtctat atgacggatg ttatatatct acgacaacag acaaggaaat tgccaagaaa   240
tttgcaacaa gttccggcat cgaaaatggc tatatatatg ttttaaatag ggatttgttt   300
ggtcaatatt ctattttga atatgggggtt gaacatccag aaaacccaaa tgagaaggaa   360
gtaacaatca gagctgaaga ttgtggctgt attcctgaag aagtgattat tgctaaagag   420
ttgatagaaa ttaac                                                   435
```

<210> SEQ ID NO 14

<211> LENGTH: 145
<212> TYPE: PRT
<213> ORGANISM: Neisseria meningitidis

<400> SEQUENCE: 14

```
Met Gly Asn Phe Leu Tyr Arg Gly Ile Ser Cys Gln Gln Asp Glu Gln
 1               5                  10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Glu Val Gly His
            100                 105                 110

Pro Glu Asn Pro Asn Glu Lys Glu Val Thr Ile Arg Ala Glu Asp Cys
        115                 120                 125

Gly Cys Ile Pro Glu Glu Val Ile Ile Ala Lys Glu Leu Ile Glu Ile
    130                 135                 140

Asn
145
```

<210> SEQ ID NO 15
<211> LENGTH: 435
<212> TYPE: DNA
<213> ORGANISM: Neisseria meningitidis

<400> SEQUENCE: 15

```
atgggaaatt tcttatatag aggcattagt tgccaacaag atgagcaaaa taatggacag     60
ttaaaaccta aagtaataa agctgaagtt gcaattcgtt atgatggtaa gtttaaatat    120
gatggtaaag ctacacatgg tccaagtgtg aagaatgcag tttacgccca tcaaattgaa    180
acaggtctat atgacggatg ttatatatct acgacaacag acaaggaaat tgccaagaaa    240
tttgcaacaa gttccggcat cgaaaatggc tatatatatg ttttaaatag ggatttgttt    300
ggtcaatatt ctattttga atatgaggtt ggacatccag aaaacccaaa tgagaaggaa    360
gtaacaatca gagctgaaga ttgtggctgt attcctgaag aagtgattat tgctaaagag    420
ttgatagaaa ttaac                                                    435
```

<210> SEQ ID NO 16
<211> LENGTH: 145
<212> TYPE: PRT
<213> ORGANISM: Neisseria meningitidis

<400> SEQUENCE: 16

```
Met Gly Asn Phe Leu Tyr Arg Gly Ile Ser Cys Gln Gln Asp Glu Gln
 1               5                  10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60
```

Asp Gly Cys Tyr Ile Ser Thr Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Glu Val Glu His
            100                 105                 110

Pro Glu Asn Pro Asn Glu Lys Gly Val Thr Ile Arg Ala Glu Asp Cys
        115                 120                 125

Gly Cys Ile Pro Glu Glu Val Ile Ile Ala Lys Glu Leu Ile Glu Ile
    130                 135                 140

Asn
145

<210> SEQ ID NO 17
<211> LENGTH: 435
<212> TYPE: DNA
<213> ORGANISM: Neisseria meningitidis

<400> SEQUENCE: 17
atgggaaatt tcttatatag aggcattagt tgccaacaag atgagcaaaa taatggacag      60
ttaaaaccta aggtaataa agctgaagtt gcaattcgtt atgatggtaa gtttaaatat     120
gatggtaaag ctacacatgg tccaagtgtg aagaatgcag tttacgccca tcaaattgaa     180
acaggtctat atgacggatg ttatatatct acgacaacag acaaggaaat tgccaagaaa     240
tttgcaacaa gttccggcat cgaaaatggc tatatatatg ttttaaatag ggatttgttt     300
ggtcaatatt ctattttga atatgaggtt gaacatccag aaaacccaaa tgagaaggga     360
gtaacaatca gagctgaaga ttgtggctgt attcctgaag aagtgattat tgctaaagag     420
ttgatagaaa ttaac                                                     435

<210> SEQ ID NO 18
<211> LENGTH: 45
<212> TYPE: DNA
<213> ORGANISM: Artificial Sequence
<220> FEATURE:
<223> OTHER INFORMATION: PCR primer

<400> SEQUENCE: 18
cgcggatccc atatgggaaa tttcttatat agaggcatta gttgc                     45

<210> SEQ ID NO 19
<211> LENGTH: 37
<212> TYPE: DNA
<213> ORGANISM: Artificial Sequence
<220> FEATURE:
<223> OTHER INFORMATION: PCR primer

<400> SEQUENCE: 19
cccgctcgag gttaatttct atcaactctt tagcaat                              37

<210> SEQ ID NO 20
<211> LENGTH: 45
<212> TYPE: DNA
<213> ORGANISM: Artificial Sequence
<220> FEATURE:
<223> OTHER INFORMATION: PCR primer

<400> SEQUENCE: 20
cgcggatccc atatgggaaa tttcttatat aaaggcatta gttgc                     45

<210> SEQ ID NO 21

```
<211> LENGTH: 33
<212> TYPE: DNA
<213> ORGANISM: Artificial Sequence
<220> FEATURE:
<223> OTHER INFORMATION: PCR primer

<400> SEQUENCE: 21
atttttgaat atggggttga acatccagaa aac                                    33

<210> SEQ ID NO 22
<211> LENGTH: 33
<212> TYPE: DNA
<213> ORGANISM: Artificial Sequence
<220> FEATURE:
<223> OTHER INFORMATION: PCR primer

<400> SEQUENCE: 22
ttctggatgt caaccccat attcaaaaat aga                                     33

<210> SEQ ID NO 23
<211> LENGTH: 27
<212> TYPE: DNA
<213> ORGANISM: Artificial Sequence
<220> FEATURE:
<223> OTHER INFORMATION: PCR primer

<400> SEQUENCE: 23
tatgaggttg gacatccaga aaaccca                                           27

<210> SEQ ID NO 24
<211> LENGTH: 27
<212> TYPE: DNA
<213> ORGANISM: Artificial Sequence
<220> FEATURE:
<223> OTHER INFORMATION: PCR primer

<400> SEQUENCE: 24
gttttctgga tgtccaacct catattc                                           27

<210> SEQ ID NO 25
<211> LENGTH: 28
<212> TYPE: DNA
<213> ORGANISM: Artificial Sequence
<220> FEATURE:
<223> OTHER INFORMATION: PCR primer

<400> SEQUENCE: 25
ccaaatgaga agggagtaac aatcagag                                          28

<210> SEQ ID NO 26
<211> LENGTH: 27
<212> TYPE: DNA
<213> ORGANISM: Artificial Sequence
<220> FEATURE:
<223> OTHER INFORMATION: PCR primer

<400> SEQUENCE: 26
gattgttact cccttctcat ttgggtt                                           27

<210> SEQ ID NO 27
<211> LENGTH: 258
<212> TYPE: PRT
<213> ORGANISM: Vibrio cholerae

<400> SEQUENCE: 27

Met Val Lys Ile Ile Phe Val Phe Phe Ile Phe Leu Ser Ser Phe Ser
 1               5                  10                  15
```

Tyr Ala Asn Asp Asp Lys Leu Tyr Arg Ala Asp Ser Arg Pro Pro Asp
                20                  25                  30

Glu Ile Lys Gln Ser Gly Gly Leu Met Pro Arg Gly Gln Ser Glu Tyr
            35                  40                  45

Phe Asp Arg Gly Thr Gln Met Asn Ile Asn Leu Tyr Asp His Ala Arg
        50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu

<210> SEQ ID NO 28
<211> LENGTH: 259
<212> TYPE: PRT
<213> ORGANISM: Escherichia coli

<400> SEQUENCE: 28

Met Lys Asn Ile Thr Phe Ile Phe Phe Ile Leu Leu Ala Ser Pro Leu
1               5                   10                  15

Tyr Ala Asn Gly Asp Arg Leu Tyr Arg Ala Asp Ser Arg Pro Pro Asp
                20                  25                  30

Glu Ile Lys Arg Ser Gly Gly Leu Met Pro Arg Gly His Asn Glu Tyr
            35                  40                  45

Phe Asp Arg Gly Thr Gln Met Asn Ile Asn Leu Tyr Asp His Ala Arg
        50                  55                  60

Gly Thr Gln Thr Gly Phe Val Arg Tyr Asp Asp Gly Tyr Val Ser Thr
65                  70                  75                  80

Ser Leu Ser Leu Arg Ser Ala His Leu Ala Gly Gln Ser Ile Leu Ser
                85                  90                  95

Gly Tyr Ser Thr Tyr Tyr Ile Tyr Val Ile Ala Thr Ala Pro Asn Met
            100                 105                 110

Phe Asn Val Asn Asp Val Leu Gly Val Tyr Ser Pro His Pro Tyr Glu
        115                 120                 125

```
Gln Glu Val Ser Ala Leu Gly Gly Ile Pro Tyr Ser Gln Ile Tyr Gly
            130                 135                 140

Trp Tyr Arg Val Asn Phe Gly Val Ile Ala Asp Glu Arg Leu His Arg
145                 150                 155                 160

Asn Arg Glu Tyr Arg Asp Arg Tyr Tyr Arg Asn Leu Asn Ile Ala Pro
                165                 170                 175

Ala Glu Asp Gly Tyr Arg Leu Ala Gly Phe Pro Pro Asp His Gln Ala
            180                 185                 190

Trp Arg Glu Glu Pro Trp Ile His His Ala Pro Gln Gly Cys Gly Asn
        195                 200                 205

Ser Ser Arg Thr Ile Thr Gly Asp Thr Cys Asn Glu Glu Thr Gln Asn
    210                 215                 220

Leu Ser Thr Ile Tyr Leu Arg Glu Tyr Gln Ser Lys Val Lys Arg Gln
225                 230                 235                 240

Ile Phe Ser Asp Tyr Gln Ser Glu Val Asp Ile Tyr Asn Arg Ile Arg
                245                 250                 255

Asp Glu Leu

<210> SEQ ID NO 29
<211> LENGTH: 264
<212> TYPE: PRT
<213> ORGANISM: Bordetella pertussis

<400> SEQUENCE: 29

Ala Ile Arg Gln Thr Ala Arg Thr Gly Trp Leu Thr Trp Leu Ala Ile
1               5                   10                  15

Leu Ala Val Thr Ala Pro Val Thr Ser Pro Ala Trp Ala Asp Asp Pro
            20                  25                  30

Pro Ala Thr Val Tyr Arg Tyr Asp Ser Arg Pro Pro Glu Asp Val Phe
        35                  40                  45

Gln Asn Gly Phe Thr Ala Trp Gly Asn Asn Asp Asn Val Leu Asp His
    50                  55                  60

Leu Thr Gly Arg Ser Cys Gln Val Gly Ser Ser Asn Ser Ala Phe Val
65                  70                  75                  80

Ser Thr Ser Ser Ser Arg Arg Tyr Thr Glu Val Tyr Leu Glu His Arg
                85                  90                  95

Met Gln Glu Ala Val Glu Ala Glu Arg Ala Gly Arg Gly Thr Gly His
            100                 105                 110

Phe Ile Gly Tyr Ile Tyr Glu Val Arg Ala Asp Asn Asn Phe Tyr Gly
        115                 120                 125

Ala Ala Ser Ser Tyr Phe Glu Tyr Val Asp Thr Tyr Gly Asp Asn Ala
    130                 135                 140

Gly Arg Ile Leu Ala Gly Ala Leu Ala Thr Tyr Gln Ser Glu Tyr Leu
145                 150                 155                 160

Ala His Arg Arg Ile Pro Pro Glu Asn Ile Arg Arg Val Thr Arg Val
                165                 170                 175

Tyr His Asn Gly Ile Thr Gly Glu Thr Thr Thr Glu Tyr Ser Asn
            180                 185                 190

Ala Arg Tyr Val Ser Gln Gln Thr Arg Ala Asn Pro Asn Pro Tyr Thr
        195                 200                 205

Ser Arg Arg Ser Val Ala Ser Ile Val Gly Thr Leu Val Arg Met Ala
    210                 215                 220

Pro Val Ile Gly Ala Cys Met Ala Arg Gln Ala Glu Ser Ser Glu Ala
225                 230                 235                 240

Met Ala Ala Trp Ser Glu Arg Ala Gly Glu Ala Met Val Leu Val Tyr
```

```
                      245                 250                 255

Tyr Glu Ser Ile Ala Tyr Ser Phe
                260

<210> SEQ ID NO 30
<211> LENGTH: 95
<212> TYPE: PRT
<213> ORGANISM: Bordetella pertussis

<400> SEQUENCE: 30

Thr Asp His Tyr Tyr Ser Asn Val Thr Ala Thr Arg Leu Leu Ser Ser
  1               5                  10                  15

Thr Asn Ser Arg Leu Cys Ala Val Phe Val Arg Ser Gly Gln Pro Val
             20                  25                  30

Ile Gly Ala Cys Thr Ser Pro Tyr Asp Gly Lys Tyr Trp Ser Met Tyr
         35                  40                  45

Ser Arg Leu Arg Lys Met Leu Tyr Leu Ile Tyr Val Ala Gly Ile Ser
     50                  55                  60

Val Arg Val His Val Ser Lys Glu Glu Gln Tyr Tyr Asp Tyr Glu Asp
 65                  70                  75                  80

Ala Thr Phe Glu Thr Tyr Ala Leu Thr Gly Ile Ser Ile Cys Asn
                 85                  90                  95

<210> SEQ ID NO 31
<211> LENGTH: 73
<212> TYPE: PRT
<213> ORGANISM: Bordetella pertussis

<400> SEQUENCE: 31

Thr Pro Val Val Ala Cys Ala Val Ser Lys Gln Ser Ile Trp Ala Pro
  1               5                  10                  15

Ser Phe Lys Glu Leu Leu Asp Gln Ala Arg Tyr Phe Tyr Ser Thr Gly
             20                  25                  30

Gln Ser Val Arg Ile His Val Gln Lys Asn Ile Trp Thr Tyr Pro Leu
         35                  40                  45

Phe Val Asn Thr Phe Ser Ala Asn Ala Leu Val Gly Leu Ser Ser Cys
     50                  55                  60

Ser Ala Thr Gln Cys Phe Gly Pro Lys
 65                  70

<210> SEQ ID NO 32
<211> LENGTH: 96
<212> TYPE: PRT
<213> ORGANISM: Bordetella pertussis

<400> SEQUENCE: 32

Met Tyr Ile Asn Lys Phe Val Pro Val Tyr Thr Leu Leu Ile Leu Ile
  1               5                  10                  15

Tyr Ser Phe Asn Ala Ser Ala Glu Trp Thr Gly Asp Asn Thr Asn Ala
             20                  25                  30

Tyr Tyr Ser Asp Glu Val Ile Ser Glu Leu His Val Gly Gln Ile Asp
         35                  40                  45

Thr Ser Pro Tyr Phe Cys Ile Lys Thr Val Lys Ala Asn Gly Ser Val
     50                  55                  60

His Gln Leu Leu His Val Arg Tyr Gln Ser Arg Ala Tyr Gly Arg Pro
 65                  70                  75                  80

Pro Leu Lys Asn Phe Leu Ile Arg Gln Asp Ile Phe Thr Val Gln Gly
                 85                  90                  95
```

<210> SEQ ID NO 33
<211> LENGTH: 250
<212> TYPE: PRT
<213> ORGANISM: Clostridium limosum

<400> SEQUENCE: 33

Met Asn Lys Leu Thr Glu Arg Val Leu Cys Val Gly Val Ser Gly Leu
1               5                   10                  15

Ile Leu Phe Ser Val Ala Ala Leu Val Gln Gly Thr Lys Lys Cys Tyr
            20                  25                  30

Ala Asn Pro Val Arg Asn Arg Ala Ala Ser Arg Val Lys Pro Tyr Ala
        35                  40                  45

Asp Ser Phe Lys Glu Phe Thr Asn Ile Asp Glu Ala Arg Ala Trp Gly
    50                  55                  60

Asp Lys Gln Phe Ala Lys Tyr Lys Leu Ser Ser Glu Lys Asn Ala
65                  70                  75                  80

Leu Thr Ile Tyr Thr Arg Asn Ala Ala Arg Ile Asn Gly Pro Leu Arg
                85                  90                  95

Ala Asn Gln Gly Asn Thr Asn Gly Leu Pro Ala Asp Ile Arg Lys Glu
            100                 105                 110

Val Glu Gln Ile Asp Lys Ser Phe Thr Lys Met Gln Thr Pro Glu Asn
        115                 120                 125

Ile Ile Leu Phe Arg Gly Asp Asp Pro Gly Tyr Leu Gly Pro Asp Phe
    130                 135                 140

Glu Asn Thr Ile Leu Asn Arg Asp Gly Thr Ile Asn Lys Ala Val Phe
145                 150                 155                 160

Glu Gln Val Lys Leu Arg Phe Lys Gly Lys Asp Arg Lys Glu Tyr Gly
                165                 170                 175

Tyr Ile Ser Thr Ser Leu Val Asn Gly Ser Ala Phe Ala Gly Arg Pro
            180                 185                 190

Ile Ile Thr Lys Phe Lys Val Leu Asp Gly Ser Lys Ala Gly Tyr Ile
        195                 200                 205

Glu Pro Ile Ser Thr Phe Lys Gly Gln Leu Glu Val Leu Leu Pro Arg
    210                 215                 220

Ser Ser Thr Tyr Thr Ile Ser Asp Met Gln Ile Ala Pro Asn Asn Lys
225                 230                 235                 240

Gln Ile Ile Ile Thr Ala Leu Leu Lys Arg
                245                 250

<210> SEQ ID NO 34
<211> LENGTH: 194
<212> TYPE: PRT
<213> ORGANISM: Staphylococcus aureus

<400> SEQUENCE: 34

Lys Trp Gly Asn Lys Leu Ile Lys Gln Ala Lys Tyr Ser Ser Asp Asp
1               5                   10                  15

Lys Ile Ala Leu Tyr Glu Tyr Thr Lys Asp Ser Ser Lys Ile Asn Gly
            20                  25                  30

Pro Leu Arg Leu Ala Gly Gly Asp Ile Asn Lys Leu Asp Ser Thr Thr
        35                  40                  45

Gln Asp Lys Val Arg Arg Leu Asp Ser Ser Ile Ser Lys Ser Thr Thr
    50                  55                  60

Pro Glu Ser Val Tyr Val Tyr Arg Leu Leu Asn Leu Asp Tyr Leu Thr
65                  70                  75                  80

Ser Ile Val Gly Phe Thr Asn Glu Asp Leu Tyr Lys Leu Gln Gln Thr

```
                     85                  90                  95
Asn Asn Gly Gln Tyr Asp Glu Asn Leu Val Arg Lys Leu Asn Asn Val
                100                 105                 110

Met Asn Ser Arg Ile Tyr Arg Glu Asp Gly Tyr Ser Ser Thr Gln Leu
            115                 120                 125

Val Ser Gly Ala Ala Val Gly Gly Arg Pro Ile Glu Leu Arg Leu Glu
        130                 135                 140

Leu Pro Lys Gly Thr Lys Ala Ala Tyr Leu Asn Ser Lys Asp Leu Thr
145                 150                 155                 160

Ala Tyr Tyr Gly Gln Gln Glu Val Leu Leu Pro Arg Gly Thr Glu Tyr
                165                 170                 175

Ala Val Gly Ser Val Glu Leu Ser Asn Asp Lys Lys Lys Ile Ile Ile
            180                 185                 190

Thr Ala

<210> SEQ ID NO 35
<211> LENGTH: 11
<212> TYPE: PRT
<213> ORGANISM: Escherichia coli

<400> SEQUENCE: 35

Lys Leu Tyr Arg Ala Asp Ser Arg Pro Pro Asp
1               5                   10

<210> SEQ ID NO 36
<211> LENGTH: 9
<212> TYPE: PRT
<213> ORGANISM: Escherichia coli

<400> SEQUENCE: 36

Leu Tyr Asp His Ala Arg Gly Thr Gln
1               5

<210> SEQ ID NO 37
<211> LENGTH: 15
<212> TYPE: PRT
<213> ORGANISM: Escherichia coli

<400> SEQUENCE: 37

Tyr Asp Asp Gly Tyr Val Ser Thr Ser Leu Ser Leu Arg Ser Ala
1               5                   10                  15

<210> SEQ ID NO 38
<211> LENGTH: 15
<212> TYPE: PRT
<213> ORGANISM: Escherichia coli

<400> SEQUENCE: 38

Ser Pro His Pro Tyr Glu Gln Glu Val Ser Ala Leu Gly Gly Ile
1               5                   10                  15

<210> SEQ ID NO 39
<211> LENGTH: 11
<212> TYPE: PRT
<213> ORGANISM: Neisseria meningitidis

<400> SEQUENCE: 39

Phe Leu Tyr Arg Gly Ile Ser Cys Gln Gln Asp
1               5                   10

<210> SEQ ID NO 40
<211> LENGTH: 9
```

```
<212> TYPE: PRT
<213> ORGANISM: Neisseria meningitidis

<400> SEQUENCE: 40

Val Tyr Ala His Gln Ile Glu Thr Gly
 1               5

<210> SEQ ID NO 41
<211> LENGTH: 15
<212> TYPE: PRT
<213> ORGANISM: Neisseria meningitidis

<400> SEQUENCE: 41

Tyr Asp Gly Cys Tyr Ile Ser Thr Thr Thr Asp Lys Glu Ile Ala
 1               5                  10                  15

<210> SEQ ID NO 42
<211> LENGTH: 15
<212> TYPE: PRT
<213> ORGANISM: Neisseria meningitidis

<400> SEQUENCE: 42

Pro Glu Asn Pro Asn Glu Lys Glu Val Thr Ile Arg Ala Glu Asp
 1               5                  10                  15

<210> SEQ ID NO 43
<211> LENGTH: 52
<212> TYPE: PRT
<213> ORGANISM: Streptomyces coelicolor

<400> SEQUENCE: 43

Thr Leu Tyr Arg Ser Asp Ser Arg Gly Pro Gln Val Val Phe Glu Glu
 1               5                  10                  15

Gly Phe His Ala Lys Asp Val Gln Asn Gly Gln Tyr Asp Val Glu Lys
             20                  25                  30

Tyr Val Leu Val Asn Gln Pro Ser Pro Tyr Val Ser Thr Ser Tyr Asp
         35                  40                  45

His Asp Leu Tyr
     50

<210> SEQ ID NO 44
<211> LENGTH: 15
<212> TYPE: PRT
<213> ORGANISM: Streptomyces coelicolor

<400> SEQUENCE: 44

His Lys Trp Ala Asp Gln Val Glu Val Ala Phe Pro Gly Gly Ile
 1               5                  10                  15

<210> SEQ ID NO 45
<211> LENGTH: 11
<212> TYPE: PRT
<213> ORGANISM: Mycoplasma pneumoniae

<400> SEQUENCE: 45

Phe Val Tyr Arg Val Asp Leu Arg Ser Pro Glu
 1               5                  10

<210> SEQ ID NO 46
<211> LENGTH: 9
<212> TYPE: PRT
<213> ORGANISM: Mycoplasma pneumoniae

<400> SEQUENCE: 46
```

Phe Phe Glu His Ile Leu Ser Thr Asn
1               5

<210> SEQ ID NO 47
<211> LENGTH: 15
<212> TYPE: PRT
<213> ORGANISM: Mycoplasma pneumoniae

<400> SEQUENCE: 47

Gly Arg Ser Tyr Phe Ile Ser Thr Ser Glu Thr Pro Thr Ala Ala
1               5                   10                  15

<210> SEQ ID NO 48
<211> LENGTH: 15
<212> TYPE: PRT
<213> ORGANISM: Mycoplasma pneumoniae

<400> SEQUENCE: 48

Thr Ser Phe Ala Tyr Gln Arg Glu Trp Phe Thr Asp Gly Pro Ile
1               5                   10                  15

<210> SEQ ID NO 49
<211> LENGTH: 11
<212> TYPE: PRT
<213> ORGANISM: Salmonella typhi

<400> SEQUENCE: 49

Phe Val Tyr Arg Val Asp Ser Thr Pro Pro Asp
1               5                   10

<210> SEQ ID NO 50
<211> LENGTH: 15
<212> TYPE: PRT
<213> ORGANISM: Salmonella typhi

<400> SEQUENCE: 50

Ser Cys Ser Gly Gly Ser Ser Asp Ser Arg Tyr Ile Ala Thr Thr
1               5                   10                  15

<210> SEQ ID NO 51
<211> LENGTH: 15
<212> TYPE: PRT
<213> ORGANISM: Salmonella typhi

<400> SEQUENCE: 51

Thr Met Met Arg Leu Gln Arg Glu Tyr Val Ser Thr Leu Ser Ile
1               5                   10                  15

<210> SEQ ID NO 52
<211> LENGTH: 11
<212> TYPE: PRT
<213> ORGANISM: Salmonella Paratyphi

<400> SEQUENCE: 52

Phe Val Tyr Arg Val Asp Ser Thr Pro Pro Asp
1               5                   10

<210> SEQ ID NO 53
<211> LENGTH: 15
<212> TYPE: PRT
<213> ORGANISM: Salmonella Paratyphi

<400> SEQUENCE: 53

Ser Cys Ser Gly Gly Ser Ser Asp Ser Arg Tyr Ile Ala Thr Thr
1               5                   10                  15

```
<210> SEQ ID NO 54
<211> LENGTH: 15
<212> TYPE: PRT
<213> ORGANISM: Salmonella Paratyphi

<400> SEQUENCE: 54

Thr Met Met Arg Leu Gln Arg Glu Tyr Val Ser Thr Leu Ser Ile
1               5                   10                  15

<210> SEQ ID NO 55
<211> LENGTH: 11
<212> TYPE: PRT
<213> ORGANISM: Streptococcus pyogenes

<400> SEQUENCE: 55

Val Val Tyr Arg Tyr Val Tyr Glu Thr Phe Leu
1               5                   10

<210> SEQ ID NO 56
<211> LENGTH: 15
<212> TYPE: PRT
<213> ORGANISM: Streptococcus pyogenes

<400> SEQUENCE: 56

Thr Lys His Ser Phe Met Ser Thr Thr Ala Leu Lys Asn Gly Ala
1               5                   10                  15

<210> SEQ ID NO 57
<211> LENGTH: 15
<212> TYPE: PRT
<213> ORGANISM: Streptococcus pyogenes

<400> SEQUENCE: 57

Ser Ala Val Pro Ser Glu Val Glu Leu Leu Phe Pro Arg Gly Cys
1               5                   10                  15

<210> SEQ ID NO 58
<211> LENGTH: 4
<212> TYPE: PRT
<213> ORGANISM: Vibrio cholerae

<400> SEQUENCE: 58

Ile Tyr Arg Ala
1

<210> SEQ ID NO 59
<211> LENGTH: 22
<212> TYPE: PRT
<213> ORGANISM: Vibrio cholerae

<400> SEQUENCE: 59

His Asp Asp Gly Tyr Val Ser Thr Ser Ile Ser Leu Arg Ser Ala His
1               5                   10                  15

Leu Val Gly Gln Thr Ile
            20

<210> SEQ ID NO 60
<211> LENGTH: 10
<212> TYPE: PRT
<213> ORGANISM: Vibrio cholerae

<400> SEQUENCE: 60

His Pro Asp Glu Gln Glu Val Ser Ala Leu
1               5                   10
```

<210> SEQ ID NO 61
<211> LENGTH: 4
<212> TYPE: PRT
<213> ORGANISM: Neisseria meningitidis

<400> SEQUENCE: 61

Leu Tyr Arg Gly
 1

<210> SEQ ID NO 62
<211> LENGTH: 19
<212> TYPE: PRT
<213> ORGANISM: Neisseria meningitidis

<400> SEQUENCE: 62

Tyr Asp Gly Cys Tyr Ile Ser Thr Thr Thr Asp Lys Glu Ile Ala Lys
 1               5                  10                  15

Lys Phe Ala

<210> SEQ ID NO 63
<211> LENGTH: 8
<212> TYPE: PRT
<213> ORGANISM: Neisseria meningitidis

<400> SEQUENCE: 63

Pro Asn Glu Lys Glu Val Thr Ile
 1               5

<210> SEQ ID NO 64
<211> LENGTH: 4
<212> TYPE: PRT
<213> ORGANISM: Escherichia coli

<400> SEQUENCE: 64

Ile Tyr Arg Ala
 1

<210> SEQ ID NO 65
<211> LENGTH: 22
<212> TYPE: PRT
<213> ORGANISM: Escherichia coli

<400> SEQUENCE: 65

Tyr Asp Asp Gly Tyr Val Ser Thr Ser Leu Ser Leu Arg Ser Ala His
 1               5                  10                  15

Leu Ala Gly Gln Ser Ile
            20

<210> SEQ ID NO 66
<211> LENGTH: 10
<212> TYPE: PRT
<213> ORGANISM: Escherichia col

<400> SEQUENCE: 66

His Pro Tyr Glu Gln Glu Val Ser Ala Leu
 1               5                  10

<210> SEQ ID NO 67
<211> LENGTH: 4
<212> TYPE: PRT
<213> ORGANISM: Escherichia coli

<400> SEQUENCE: 67

Phe Phe Arg Ala
 1

<210> SEQ ID NO 68
<211> LENGTH: 22
<212> TYPE: PRT
<213> ORGANISM: Escherichia coli

<400> SEQUENCE: 68

Tyr Asn Asp Gly Tyr Val Ser Thr Thr Val Thr Leu Arg Gln Ala His
1               5                   10                  15

Leu Ile Gly Gln Asn Ile
            20

<210> SEQ ID NO 69
<211> LENGTH: 10
<212> TYPE: PRT
<213> ORGANISM: Escherichia coli

<400> SEQUENCE: 69

Tyr Pro Ser Glu Asn Glu Phe Ala Ala Leu
1               5                   10

<210> SEQ ID NO 70
<211> LENGTH: 4
<212> TYPE: PRT
<213> ORGANISM: Bordetella pertussis

<400> SEQUENCE: 70

Val Tyr Arg Tyr
1

<210> SEQ ID NO 71
<211> LENGTH: 21
<212> TYPE: PRT
<213> ORGANISM: Bordetella pertussis

<400> SEQUENCE: 71

Phe Val Ser Thr Ser Ser Ser Arg Arg Tyr Thr Glu Val Tyr Leu Glu
1               5                   10                  15

His Arg Met Gln Glu
            20

<210> SEQ ID NO 72
<211> LENGTH: 7
<212> TYPE: PRT
<213> ORGANISM: Bordetella pertussis

<400> SEQUENCE: 72

Thr Tyr Gln Ser Glu Tyr Leu
1               5

<210> SEQ ID NO 73
<211> LENGTH: 21
<212> TYPE: PRT
<213> ORGANISM: Pseudomonas aeruginosa

<400> SEQUENCE: 73

Asp Asp Gly Tyr Leu Ser Thr Ser Leu Asn Pro Gly Val Ala Arg Ser
1               5                   10                  15

Gly Gln Gly Thr Ile
            20

<210> SEQ ID NO 74
<211> LENGTH: 9

```
<212> TYPE: PRT
<213> ORGANISM: Pseudomonas aeruginosa

<400> SEQUENCE: 74

Tyr Lys Asn Glu Lys Glu Ile Leu Tyr
 1               5

<210> SEQ ID NO 75
<211> LENGTH: 4
<212> TYPE: PRT
<213> ORGANISM: Clostridium botulinum

<400> SEQUENCE: 75

Ala Tyr Arg Arg
 1

<210> SEQ ID NO 76
<211> LENGTH: 14
<212> TYPE: PRT
<213> ORGANISM: Clostridium botulinum

<400> SEQUENCE: 76

Ser Phe Ser Thr Ser Leu Lys Ser Thr Pro Leu Ser Phe Ser
 1               5                  10

<210> SEQ ID NO 77
<211> LENGTH: 8
<212> TYPE: PRT
<213> ORGANISM: Clostridium botulinum

<400> SEQUENCE: 77

Asp Glu Gln Glu Ile Leu Leu Asn
 1               5

<210> SEQ ID NO 78
<211> LENGTH: 4
<212> TYPE: PRT
<213> ORGANISM: Clostridium botulinum

<400> SEQUENCE: 78

Leu Phe Arg Gly
 1

<210> SEQ ID NO 79
<211> LENGTH: 15
<212> TYPE: PRT
<213> ORGANISM: Clostridium botulinum

<400> SEQUENCE: 79

Gly Tyr Ile Ser Thr Ser Leu Met Ser Ala Gln Phe Gly Gly Arg
 1               5                  10                  15

<210> SEQ ID NO 80
<211> LENGTH: 10
<212> TYPE: PRT
<213> ORGANISM: Clostridium botulinum

<400> SEQUENCE: 80

Phe Pro Gly Gln Leu Glu Val Leu Leu Pro
 1               5                  10

<210> SEQ ID NO 81
<211> LENGTH: 4
<212> TYPE: PRT
<213> ORGANISM: Clostridium limosum
```

```
<400> SEQUENCE: 81

Ile Phe Arg Gly
 1

<210> SEQ ID NO 82
<211> LENGTH: 15
<212> TYPE: PRT
<213> ORGANISM: Clostridium limosum

<400> SEQUENCE: 82

Gly Tyr Ile Ser Thr Ser Leu Met Asn Val Ser Gln Phe Ala Gly
 1               5                  10                  15

<210> SEQ ID NO 83
<211> LENGTH: 10
<212> TYPE: PRT
<213> ORGANISM: Clostridium limosum

<400> SEQUENCE: 83

Phe Ala Gly Gln Leu Glu Met Leu Leu Pro
 1               5                  10

<210> SEQ ID NO 84
<211> LENGTH: 4
<212> TYPE: PRT
<213> ORGANISM: Clostridium limosum

<400> SEQUENCE: 84

Leu Phe Arg Gly
 1

<210> SEQ ID NO 85
<211> LENGTH: 16
<212> TYPE: PRT
<213> ORGANISM: Clostridium limosum

<400> SEQUENCE: 85

Gly Tyr Ile Ser Thr Ser Leu Val Asn Gly Ser Ala Phe Ala Gly Arg
 1               5                  10                  15

<210> SEQ ID NO 86
<211> LENGTH: 10
<212> TYPE: PRT
<213> ORGANISM: Clostridium limosum

<400> SEQUENCE: 86

Phe Lys Gly Gln Leu Glu Val Leu Leu Pro
 1               5                  10

<210> SEQ ID NO 87
<211> LENGTH: 4
<212> TYPE: PRT
<213> ORGANISM: Clostridium perfringens

<400> SEQUENCE: 87

Val Tyr Arg Arg
 1

<210> SEQ ID NO 88
<211> LENGTH: 19
<212> TYPE: PRT
<213> ORGANISM: Clostridium perfringens

<400> SEQUENCE: 88

Phe Ile Ser Thr Ser Ile Gly Ser Val Asn Met Ser Ala Phe Ala Lys
```

Arg Lys Ile

<210> SEQ ID NO 89
<211> LENGTH: 9
<212> TYPE: PRT
<213> ORGANISM: Clostridium perfringens

<400> SEQUENCE: 89

Tyr Ala Gly Glu Tyr Glu Val Leu Leu
 1               5

<210> SEQ ID NO 90
<211> LENGTH: 10
<212> TYPE: PRT
<213> ORGANISM: Bacillus cereus

<400> SEQUENCE: 90

Tyr Pro Gly Gln Tyr Glu Leu Leu Leu Pro
 1               5                  10

<210> SEQ ID NO 91
<211> LENGTH: 4
<212> TYPE: PRT
<213> ORGANISM: Staphylococcus aureus

<400> SEQUENCE: 91

Val Tyr Arg Leu
 1

<210> SEQ ID NO 92
<211> LENGTH: 16
<212> TYPE: PRT
<213> ORGANISM: Staphylococcus aureus

<400> SEQUENCE: 92

Gly Tyr Ser Ser Thr Gln Leu Val Ser Gly Ala Ala Val Gly Gly Arg
 1               5                  10                  15

<210> SEQ ID NO 93
<211> LENGTH: 10
<212> TYPE: PRT
<213> ORGANISM: Staphylococcus aureus

<400> SEQUENCE: 93

Tyr Tyr Gly Gln Gln Glu Val Leu Leu Pro
 1               5                  10

<210> SEQ ID NO 94
<211> LENGTH: 5
<212> TYPE: PRT
<213> ORGANISM: Corynebacterium diphtheriae

<400> SEQUENCE: 94

Ser Tyr His Gly Thr
 1               5

<210> SEQ ID NO 95
<211> LENGTH: 16
<212> TYPE: PRT
<213> ORGANISM: Corynebacterium diphtheriae

<400> SEQUENCE: 95

Trp Lys Gly Phe Tyr Ser Thr Asp Asn Lys Tyr Asp Ala Ala Gly Tyr
 1               5                  10                  15

```
<210> SEQ ID NO 96
<211> LENGTH: 4
<212> TYPE: PRT
<213> ORGANISM: Corynebacterium diphtheriae

<400> SEQUENCE: 96

Glu Tyr Ile Asn
 1

<210> SEQ ID NO 97
<211> LENGTH: 5
<212> TYPE: PRT
<213> ORGANISM: Pseudomonas aeruginosa

<400> SEQUENCE: 97

Gly Tyr His Gly Thr
 1               5

<210> SEQ ID NO 98
<211> LENGTH: 16
<212> TYPE: PRT
<213> ORGANISM: Pseudomonas aeruginosa

<400> SEQUENCE: 98

Trp Arg Gly Phe Tyr Ile Ala Gly Asp Pro Ala Leu Ala Tyr Gly Tyr
 1               5                  10                  15

<210> SEQ ID NO 99
<211> LENGTH: 4
<212> TYPE: PRT
<213> ORGANISM: Pseudomonas aeruginosa

<400> SEQUENCE: 99

Glu Thr Ile Leu
 1
```